US008106166B2

(12) United States Patent
He et al.

(10) Patent No.: US 8,106,166 B2
(45) Date of Patent: Jan. 31, 2012

(54) ANTIBODIES THAT BIND SPECIFICALLY TO PHOSPHORYLATED β-CATENIN

(75) Inventors: Xi He, Leawood, KS (US); Tong Yin, Prairie Village, KS (US); Qiang Tian, Seattle, WA (US); Weiguo Tao, West Lafayette, IN (US); Leroy Hood, Seattle, WA (US); Linheng Li, Leawood, KS (US)

(73) Assignee: Stowers Institute for Medical Research, Kansas City, MO (US)

( * ) Notice: Subject to any disclaimer, the term of this patent is extended or adjusted under 35 U.S.C. 154(b) by 108 days.

(21) Appl. No.: 12/077,290

(22) Filed: Mar. 17, 2008

(65) Prior Publication Data
US 2008/0248026 A1    Oct. 9, 2008

Related U.S. Application Data

(60) Provisional application No. 60/895,204, filed on Mar. 16, 2007.

(51) Int. Cl.
*C07K 16/26* (2006.01)
*C07K 16/00* (2006.01)

(52) U.S. Cl. ............. 530/388.24; 530/388.1; 530/387.9; 530/387.1; 435/810

(58) Field of Classification Search ........................ None
See application file for complete search history.

(56) References Cited

U.S. PATENT DOCUMENTS

| 4,931,385 A * | 6/1990 | Block et al. ................. 435/7.94 |
| 2005/0271638 A1 | 12/2005 | Li et al. |

OTHER PUBLICATIONS

Campbell Monoclonal Antibody Technology, 1984, Chapter 1, pp. 1-32.*
Aberle et al., "B-Catenina Is a Target for the Ubiquitin-Proteasome Pathway," EMBO J., vol. 16, pp. 3797-3804 (1997).
Akashi et al., "Transcriptional Accessibility for Genes of Multiple Tissues and Hematopoietic Lineages Is Hierarchically Controlled During Early Hematopoiesis," Blood, vol. 101, pp. 383-390 (2003).
Al-Hajj et al., "Prospective Identification of Tumorigenic Breast Cancer Cells," Proc. Natl. Acad. Sci. U.S.A., vol. 100, pp. 3983-3988 (2003).
Altschul et al. "Basic Local Alignment Search Tool," J. Mol. Biol., 215, pp. 403-410 (1990).
Altschul et al., "Gapped BLAST and PSI-BLAST: A New Generation of Protein Database Search Programs," Nucleic Acids Res., vol. 25, No. 17, pp. 3389-3402. (1997).
Asai et al., "Correlation Between Musashi-1 and c-hairy-1 Expression and Cell Proliferation Activity in the Developing Intestine and Stomach of Both Chicken and Mouse," Develop. Growth Differ., 47, pp. 501-510 (2005).
Bei et al, "FGFs and BMP4 Induce Both Msx1-Independent and Msx1-Dependent Signaling Pathways in Early Tooth Development," Development 125, pp. 4325-4333 (1998).

Belletti et al. "Regulation of Id2 Gene Expression by the Insulin-Like Growth Factor I Receptor Requires Signaling by Phosphatidylinositol 3-Kinase,". J. Biol. Chem., vol. 276, No. 17, pp. 13867-13874 (2001).
Bitgood et al., "Hedgehog and Bmp Genes Are Coexpressed At Many Diverse Sites of Cell-Cell Interaction in the Mouse Embryo," Developmental Biology, 172, pp. 126-138 (1995).
Bjerknes et al., "Clonal Analysis of Mouse Intestinal Epithelial Progenitors,"Gastroenterology, 116, pp. 7-14 (1999).
Booth et al., "Gut Instincts: Thoughts on Intestinal Epithelial Stem Cells," J. Clin. Invest., vol. 105, No. 11, pp. 1493-1499 (2000).
Brittan et al., "Gastrointestinal Stem Cells," J. Pathol., 197, pp. 492-509 (2002).
Campbell, "Selection of Animals and Cell Lines," Laboratory Techniques in Biochemistry and Molecular Biology—Monoclonal Antibody Technology, vol. 13, pp. 75-83, (1984).
Clement et al., "Bone Morphogenetic Protein 2 (BMP-2) Induces Sequential Changes of Id Gene Expression in the Breast Cancer Cell Line MCF-7," J. Cancer Res. Clin. Oncol., 126, pp. 271-279 (2000).
Cotsarelis et al, "Label-Retaining Cells Reside in the Bulge Area of Pilosebaceous Unit: Implications for Follicular Stem Cells, Hair Cycle, and Skin Carcinogenesis," Cell, vol. 61, pp. 1329-1337 (1990).
Crawford, "The Gastrointestinal Tract," Robbins Pathologic Basis of Diease, 6th Ed., pp. 775-843 (1999).
Cully et al, "Beyond PTEN Mutations: The PI3K Pathway As an Integrator of Multiple Inputs During Tumorigenesis," Nature Rev. Cancer, vol. 6, pp. 184-192 (2006).
Dale et al., "A Gradient of BMP Activity Specifies Dorsal-Ventral Fates in Early *Xenopus* Embryos," Cell & Developmental Biology, vol. 10, pp. 39-326 (1999).
Datta et al, "Akt Phosphorylation of BAD Couples Survival Signals to the Cell-Intrinsic Death Machinery," Cell, vol. 91, pp. 231-241 (1997).
Datta et al., "14-3-3 Proteins and Survival Kinases Cooperate to Inactivate BAD by BH3 Domain Phosphorylation," Molecular Cell, vol. 6, pp. 41-51 (2000).
Deng et al., "Spectrosomes and Fusomes Anchor Mitotic Spindles During Asymmetric Germ Cell Divisions and Facilitate the Formation of a Polarized Microtubule Array for Oocyte Specification in *Drosophila*," Developmental Biology, 189, pp. 79-94 (1997).
Entchev et al., "Gradient Formation of the TGF-β Homolog Dpp," Cell, vol. 103, pp. 981-991 (2000). Fero et al., "A Syndrome of Multiorgan Hyperplasia With Features of Gigantism, Tumorigenesis, and Female Sterility in p27Kip1-Deficient Mice," Cell, vol. 85, pp. 733-744 (1996).
Fuchs et al., "At the Roots of a Never-Ending Cycle," Developmental Cell, vol. 1, pp. 13-25 (2001).
Fukumoto et al., "Akt Participation in the Wnt Signaling Pathway Through Dishevelled," J. Biol. Chem., vol. 276, No. 20, pp. 17479-17483 (2001).
Gefter et al., "A Simple Method for Polyethylene Glycol-Promoted Hybridization of Mouse Myeloma Cells," Somatic Cell Genetics, vol. 3, No. 2, pp. 231-236 (1977).

(Continued)

*Primary Examiner* — Sharon Wen
(74) *Attorney, Agent, or Firm* — Bryan Cave LLP

(57) ABSTRACT

The present invention relates to a purified molecules, including antibodies, that bind specifically to murine β-catenin phosphorylated at amino acid position Serine$^{552}$ and to orthologs thereof, such as mammalian orthologs, including human orthologs. Methods of making and using such purified molecules are also provided. Kits containing such purified molecules are further provided.

15 Claims, 13 Drawing Sheets
(12 of 13 Drawing Sheet(s) Filed in Color)

OTHER PUBLICATIONS

Gera et al., "AKT Activity Determines Sensitivity to Mammalian Target of Rapamycin (mTOR) Inhibitors by Regulating Cyclin D1 and c-myc Expression," J. Biol. Chem., vol. 270, No. 4, pp. 2737-2746 (2004).
Fero et al., "A Syndrome of Multiorgan Hyperplasia With Features of Gigantism, Tumorigenesis, and Female Sterility in p27Kip1-Deficient Mice," Cell, vol. 85, pp. 733-744 (1996).
Fuchs et al., "At the Roots of a Never-Ending Cycle," Developmental Cell, vol. 1, pp. 13-25 (2001).
Fukumoto et al., "Akt Participation in the Wnt Signaling Pathway Through Dishevelled," J. Biol. Chem., vol. 276, No. 20, pp. 17479-17483 (2001).
Gefter et al., "A Simple Method for Polyethylene Glycol-Promoted Hybridization of Mouse Myeloma Cells," Somatic Cell Genetics, vol. 3, No. 2, pp. 231-236 (1977).
Gera et al., "AKT Activity Determines Sensitivity to Mammalian Target of Rapamycin (mTOR) Inhibitors by Regulating Cyclin D1 and c-myc Expression," J. Biol. Chem., vol. 270, No. 4, pp. 2737-2746 (2004).
Ghosh-Choudhury et al., "Requirement of BMP-2-induced Phosphatidylinositol 3-Kinase and Akt Serine/Threonine Kinase in Osteoblast Differentiation and Smad-Dependent BMP-2 Gene Transcription," J. Biol. Chem., vol. 277, No. 36, pp. 33361-33368 (2002).
Goding, "Production of Monoclonal Antibodies," Monoclonal Antibodies: Principles and Practice, 2nd Ed., Academic Press, pp. 59-61, 64-67, 70-75 (1986).
Gottardi et al., "Distinct Molecular Forms of β-Catenin Are Targeted to Adhesive or Transcriptional Complexes," J. Cell Biol., vol. 167, No. 2, pp. 339-349 (2004).
Greaves et al., "Mitochondrial DNA Mutations Are Established in Human Colonic Stem Cells, and Mutated Clones Expand by Crypt Fission," Proc. Natl. Acad. Sci. U.S.A., vol. 103, No. 3, pp. 714-719 (2006).
Gregorieff et al, "Expression Pattern of Wnt Signaling Components in the Adult Intestine," Gastroenterology, vol. 129, No. 2, pp. 626-638 (2005).
Grossmann et al., "New Isolation Technique to Study Apoptosis in Human Intestinal Epithelial Cells," Am. J. Pathol., vol. 153, No. 1, pp. 53-62 (1998).
Groszer et al., "Negative Regulation of Neural Stem/Progenitor Cell Proliferation by the PTEN Tumor Suppressor Gene In Vivo," Science, vol. 294, pp. 2186-2189 (2001).
Groszer et al., "PTEN Negatively Regulates Neural Stem Cell Self-Renewal by Modulating G0-G1 Cell Cycle Entry," Proc. Natl. Acad. Sci. USA, vol. 103, No. 1, pp. 111-116 (2006).
Guatelli et al., "Isothermal, In Vitro Amplification of Nucleic Acids by a Multienzyme Reaction Modeled After Retroviral Replication," Proc. Natl. Acad. Sci. USA, vol. 87, pp. 1874-1878 (1990).
Haramis et al., "De Novo Crypt Formation and Juvenile Polyposis on BMP Inhibition in Mouse Intestine," Science, vol. 303, pp. 1684-1686 (2004).
He et al., "PTEN-Deficient Intestinal Stem Cells Initiate Intestinal Polyposis," Nature Genetics, vol. 39, No. 2, pp. 189-198 (2007).
He et al., "BMP Signaling Inhibits Intestinal Stem Cell Self-Renewal Through Suppression of Wnt-β-Catenin Signaling," Nature Genetics, vol. 36, No. 10, pp. 1117-1121 (2004).
Hefferan et al., "Overexpression of a Nuclear Protein, TIEG, Mimics Transforming Growth Factor-B Action in Human Osteoblast Cells," J. Biol. Chem., vol. 275, No. 27, pp. 20255-20259 (2000).
Hermiston et al., "Organization of the Crypt-Villus Axis and Evolution of Its Stem Cell Hierarchy During Intestinal Development," American Physiological Society, 268, pp. G813-G822 (1995).
Hogan, "Bone Morphogenetic Proteins in Development," Current Opinion in Genetics & Development, 6, pp. 432-438 (1996).
Houlston et al., "Mutations in DPC4 (SMAD4) Cause Juvenile Polyposis Syndrome, But Only Account for a Minority of Cases," Human Molecular Genetics, vol. 7, No. 12, pp. 1907-1912 (1998).
Howe et al., "Mutations in the SMAD4/DPC4 Gene in Juvenile Polyposis," Science, vol. 280, pp. 1086-1088 (1998).
Howe et al., "Germline Mutations of the Gene Encoding Bone Morphogenetic Protein Receptor 1A in Juvenile Polyposis," Nature Genetics, vol. 28, pp. 184-187 (2001).
Hu et al., "Msx Homeobox Genes Inhibit Differentiation Through Upregulation of Cyclin D1," Development, 128, pp. 2373-2384 (2001).
Hu et al., "Multilineage Gene Expression Precedes Commitment in the Hemopoietic System," Genes & Development, 11, pp. 774-785 (1997).
Huber et al., "Three-Dimensional Structure of the Armadillo Repeat Region of B-Catenin," Cell, vol. 90, pp. 871-882 (1997).
Hurlstone, "T-Cell Factors: Turn-Ons and Turn-Offs," EMBO J., vol. 21, No. 10, pp. 2303-2311 (2002).
Itoh et al., "Signaling of Transforming Growth Factor-B Family Members Through Smad Proteins," Eur. J. Biochem., 267, pp. 6954-6967 (2000).
Itoh et al., "Activation of Immediate Early Gene, c-fos, and c-jun in the Rat Small Intestine After Ischemia/Reperfusion," Transplantation, vol. 69, No. 4, pp. 598-604 (2000).
Kandel et al., "The Regulation and Activities of the Multifunctional Serine/Threonine Kinase Akt/PKB," Experimental Cell Research, 253, pp. 210-229 (1999).
Kang et al., "Akt Protein Kinase Enhances Human Telomerase Activity Through Phosphorylation of Telomerase Reverse Transcriptase Subunit," J. Biol. Chem., vol. 274, No. 19, pp. 13085-13090 (1999).
Karlin et al., "Methods for Assessing the Statistical Significance of Molecular Sequence Features by Using General Scoring Schemes," Proc. Natl. Acad. Sci. USA, vol. 87, pp. 2264-2268 (1990).
Khatri et al., "Profiling Gene Expression Using Onto-Express," Genomics, vol. 79, No. 2, pp. 266-270 (2002).
Khwaja et al., "Matrix Adhesion and Ras Transformation Both Activate a Phosphoinositide 3-OH Kinase and Protein Kinase B/Akt Cellular Survival Pathway," EMBO J., vol. 16, No. 10, pp. 2783-2793 (1997).
Kimura et al, "Conditional Loss of PTEN Leads to Testicular Teratoma and Enhances Embryonic Germ Cell Production," Development, 130, pp. 1691-1700 (2003).
King et al., "Krüppel-Like Factor 4 (KLF4/GKLF) Is a Target of Bone Morphogenetic Proteins and Transforming Growth Factor β1 in the Regulation of Vascular Smooth Muscle Cell Phenotype," J. Biol. Chem., vol. 278, No. 13, pp. 11661-11669 (2003).
Kobayashi et al., "Regulation of Inhibin β Chains and Follistatin mRNA Levels During Rat Hepatocyte Growth Induced by the Peroxisome Proliferator Di-n-Butyl Phthalate," Biol. Pharm. Bull., vol. 25, No. 9, pp. 1214-1216 (2002).
Köhler et al., "Continuous Cultures of Fused Cells Secreting Antibody of Predefined Specificity," Nature, vol. 256, pp. 495-497 (1975).
Köhler et al., "Derivation of Specific Antibody-Producing Tissue Culture and Tumor Lines By Cell Fusion," Eur. J. Immunol., 6, pp. 511-519 (1976).
Koike et al, "β-Catenin Shows an Overlapping Sequence Requirement But Distinct Molecular Interactions for Its Bidirectional Passage Through Nuclear Pores," J. Biol. Chem., vol. 279, No. 32, pp. 34038-34047 (2004).
Korinek et al., "Depletion of Epithelial Stem-Cell Compartments in the Small Intestine of Mice Lacking Tcf-4," Nature Genetics, vol. 19, pp. 379-383 (1998).
Kuhn et al., "Inducible Gene Targeting in Mice," Science, vol. 269, pp. 1427-1429 (1995).
Kwoh et al., "Transcription-Based Amplification System and Detection of Amplified Human Immunodeficiency Virus Type 1 With a Bead-Based Sandwich Hybridization Format," Proc. Natl. Acad. Sci. USA, vol. 86, pp. 1173-1177 (1989).
Lapidot et al., "A Cell Initiating Human Acute Myeloid Leukaemia After Transplantation Into SCID Mice," Nature, vol. 367, pp. 645-648 (1994).
Liaw et al., "Germline Mutations of the PTEN Gene in Cowden Disease, an Inherited Breast and Thyroid Cancer Syndrome," Nature Genetics, vol. 16, No. 1, pp. 64-67 (1997).
Lim et al., "Noggin Antagonizes BMP Signaling to Create a Niche for Adult Neurogenesis," Neuron, vol. 28, pp. 713-726 (2000).
Lin et al., "Prostate-Localized and Androgen-Regulated Expression of the Membrane-Bound Serine Protease TMPRSS2," Cancer Research, 59, pp. 4180-4184 (1999).

Lowry et al., "Defining the Impact of β-Catenin/Tcf Transactivation on Epithelial Stem Cells," Genes & Development, 19, pp. 1596-1611 (2005).

Luongo et al., "Loss of Apc+ in Intestinal Adenomas From Min Mice," Cancer Research, 54, pp. 5947-5952 (1994).

Maehama et al., "The Tumor Suppressor, PTEN/MMAC1, Dephosphorylates the Lipid Second Messenger, Phosphatidylinositol 3,4,5-Trisphosphate," J. Biol. Chem., vol. 273, No. 22, pp. 13375-13378 (1998).

Massagué, "TGF-β Signal Transduction," Annu. Rev. Biochem. 67, pp. 753-791 (1998).

McMahon et al., "Noggin-Mediated Antagonism of BMP Signaling Is Required for Growth and Patterning of the Neural Tube and Somite," Genes & Development, 12, pp. 1438-1452 (1998).

Megy et al., "Solution Structure of a Peptide Derived From the Oncogenic Protein β-Catenin in Its Phosphorylated and Nonphosphorylated States," Peptides, 26, pp. 227-241 (2005).

Mishina et al., "Bmpr Encodes a Type I Bone Morphogenetic Protein Receptor That Is Essential for Gastrulation During Mouse Embryogenesis," Genes & Development, 9, pp. 3027-3037 (1995).

Mishina et al., "Generation of Bmpr/Alk3 Conditional Knockout Mice," Genesis, 32, pp. 69-72 (2002).

Morrison et al., "Telomerase Activity in Hematopoietic Cells Is Associated With Self-Renewal Potential," Immunity, vol. 5, pp. 207-216 (1996).

Munishkin et al., "An in Vivo Recombinant RNA Capable of Autocatalytic Synthesis by Qβ Replicase," Nature, vol. 333, pp. 473-475 (1988).

Nagasako et al., "Up-regulated Smad5 mediates apoptosis of gastric epithelial cells induced by *Helicobacter pylori* infection," J. Biol. Chem., vol. 278, No. 7, pp. 4821-4825 (2003).

Nakamura et al., "Accumulation of p27KIP1 Is Associated With BMP2-Induced Growth Arrest and Neuronal Differentiation of Human Neuroblastoma-Derived Cell Lines," Biochemical and Biophysical Research Communications, 307, pp. 206-213 (2003).

Novak et al., Z/EG, a Double Reporter Mouse Line That Expresses Enhanced Green Fluorescent Protein Upon Cre-Mediated Excision, Genesis, 28, pp. 147-155 (2000).

Passegué et al., "JunB Deficiency Leads to a Myeloproliferative Disorder Arising From Hematopoietic Stem Cells," Cell, vol. 119, pp. 431-443 (2004).

Penninger et al., "PTEN—Coupling Tumor Suppression to Stem Cells?" Science, vol. 294, pp. 2116-2118 (2001).

Persad et al., "Tumor Suppressor PTEN Inhibits Nuclear Accumulation of β-Catenin and T Cell/Lymphoid Enhancer Factor 1-Mediated Transcriptional Activation," J. Cell Biol., vol. 153, No. 6, 1161-1173 (2001).

Piedra et al., "Regulation of β-Catenin Structure and Activity by Tyrosine Phosphorylation," J. Biol. Chem., vol. 276, No. 23, pp. 20436-20443 (2001).

Polakis, "Wnt Signaling and Cancer," Genes & Development, 14, pp. 1837-1851 (2000).

Potten et al., "Keratinocyte Stem Cells: A Commentary," J. Invest. Dermatol., vol. 119, No. 4, pp. 888-899 (2002).

Potten et al., "Identification of a Putative Intestinal Stem Cell and Early Lineage Marker; Musashi-1," Differentiation, 71, pp. 28-41 (2003).

Potten et al., "Intestinal Stem Cells Protect Their Genome by Selective Segregation of Template DNA Strands," J. Cell Sci., 115, pp. 2381-2388 (2002).

Powell et al., "APC Mutations Occur Early During Colorectal Tumorigenesis," Nature, vol. 359, pp. 235-237 (1992).

Prendergast et al., "A New Bind for Myc," Trends in Genetics, vol. 8, pp. 91-96 (1992).

Preston et al., "Bottom-Up Histogenesis of Colorectal Adenomas: Origin in the Monocryptal Adenoma and Initial Expansion by Crypt Fission," Cancer Research, 63, pp. 3819-3825 (2003).

Quaroni et al., "p27Kip1 Is an Inducer of Intestinal Epithelial Cell Differentiation," Am. J. Physiol. Cell Physiol., 279, C1045-C1057 (2000).

Radtke et al., "Self-Renewal and Cancer of the Gut: Two Sides of a Coin," Science, vol. 307, pp. 1904-1909 (2005).

Ray et al., "Inducible Expression of Keratinocyte Growth Factor (KGF) in Mice Inhibits Lung Epithelial Cell Death Induced by Hyperoxia," Proc. Natl. Acad. Sci. U.S.A., vol. 100, No. 10, pp. 6098-6103 (2003).

Reya et al., "Stem Cells, Cancer, and Cancer Stem Cells," Nature, vol. 414, pp. 105-111 (2001).

Roberts, "Molecular Mechanisms of Development of the Gastrointestinal Tract," Developmental Dynamics, 219, pp. 109-120 (2000).

Sancho et al., "Signaling Pathways in Intestinal Development and Cancer," Annu. Rev. Cell Dev. Biol., vol. 20, pp. 695-723 (2004).

Sharma et al., "Phosphatidylinositol 3-Kinase/Akt Stimulates Androgen Pathway Through GSK3β Inhibition and Nuclear β-Catenin Accumulation," J. Biol. Chem., vol. 277, No. 34, pp. 30935-30941 (2002).

Shih et al., "Top-Down Morphogenesis of Colorectal Tumors," Proc. Natl. Acad. Sci. U.S.A., vol. 98, No. 5, pp. 2640-2645 (2001).

Singh et al., "Identification of Human Brain Tumour Initiating Cells," Nature, vol. 432, pp. 396-401 (2004).

Spradling et al., "Stem cells find their niche," Nature, vol. 414, pp. 98-104 (2001).

Stiles et al, "PTENless Means More," Developmental Biology, 273, pp. 175-184 (2004).

Tao et al., "Quantitative Phosphoproteome Analysis Using a Dendrimer Conjugation Chemistry and Tandem Mass Spectrometry," Nature Methods, vol. 2, No. 8, pp. 591-598 (2005).

Taurin et al., "Phosphorylation of β-Catenin by Cyclic AMP-Dependent Protein Kinase," J. Biol. Chem., vol. 281 No. 15, pp. 9971-9976 (2006).

Teleman et al., "Dpp Gradient Formation in the *Drosophila* Wing Imaginal Disc," Cell, vol. 103, pp. 971-980 (2000).

Tetsu et al., "β-Catenin Regulates Expression of Cyclin D1 in Colon Carcinoma Cells," Nature, vol. 398, pp. 422-426 (1999).

Tian et al., "Proteomic Analysis Identifies That 14-3-3ζ Interacts With β Catenin and Facilitates Its Activation by Akt," Proc. Natl. Acad. Sci. U.S.A., vol. 101, pp. 15370-15375 (2004).

Travers, "Priming the Nucleosome: A Role for HMGB Proteins?" EMBO Reports, vol. 4, No. 2, pp. 131-136 (2003).

Van De Wetering et al., "The β-Catenin/TCF-4 Complex Imposes a Crypt Progenitor Phenotype on Colorectal Cancer Cells," Cell, vol. 111, pp. 241-250 (2002).

Van Noort et al., "Wnt Signaling Controls the Phosphorylation Status of β Catenin," J. Biol. Chem., vol. 277, No. 22, pp. 17901-17905 (2002).

Vazquez et al., "Phosphorylation of the PTEN Tail Regulates Protein Stability and Function," Molecular and Cellular Biology, vol. 20, No. 14, pp. 5010-5018 (2000).

Vazquez et al., "Phosphorylation of the PTEN Tail Acts As an Inhibitory Switch by Preventing Its Recruitment Into a Protein Complex," J. Biol. Chem., vol. 276, No. 52, pp. 48627-48630 (2001).

Waite et al., BMP2 Exposure Results in Decreased PTEN Protein Degradation and Increased PTEN Levels, Human Molecular Genetics, vol. 12, No. 6, pp. 679-684 (2003).

Wasan et al., "APC in the Regulation of Intestinal Crypt Fission," J. Pathol., vol. 185, pp. 246-255 (1998).

Weissman, "Developmental Switches in the Immune System," Cell, vol. 76, 207-218 (1994).

Wice et al., "Forced Expression of Id-1 in the Adult Mouse Small Intestinal Epithelium Is Associated With Development of Adenomas," J. Biol. Chem., vol. 273, No. 39, pp. 25310-25319 (1998).

Wilson et al., "Expression of Id Helix-Loop-Helix Proteins in Colorectal Adenocarcinoma Correlates With p53 Expression and Mitotic Index," Cancer Research, 61, pp. 8803-8810 (2001).

Wong et al., "BMP-2 Inhibits Proliferation of Human Aortic Smooth Muscle Cells Via p21Cip1/Waf1," Am. J. Physiol. Endocrinol. Metab., vol. 284, E972-E979 (2003).

Wong et al., "Histogenesis of Human Colorectal Adenomas and Hyperplastic Polyps: The Role of Cell Proliferation and Crypt Fission," Gut, vol. 50, No. 2, pp. 212-217 (2002).

Wu et al., "PTEN Signaling Pathways in Melanoma," Oncogene, 22, pp. 3113-3122 (2003).

Yamashita et al., "Orientation of Asymmetric Stem Cell Division by the APC Tumor Suppressor and Centrosome," Science, vol. 301, pp. 1547-1550 (2003).

Yi et al., "The Type I BMP Receptor BMPRIB Is Required for Chondrogenesis in the Mouse Limb," Development, 127, pp. 621-630 (2000).

Yilmaz et al., "PTEN Dependence Distinguishes Haematopoietic Stem Cells From Leukaemia-Initiating Cells," Nature, vol. 441, pp. 475-482 (2006).

Zhang et al., "Dissection of Promoter Control Modules That Direct Bmp4 Expression in the Epithelium-Derived Components of Hair Follicles," Biochem. Biophys. Res. Commun., 293, pp. 1412-1419 (2002).

Zhang et al., "Identification of the Haematopoietic Stem Cell Niche and Control of the Niche Size," Nature, vol. 425(6960), pp. 836-841 (2003).

Zhang et al., "PTEN Maintains Hematopoietic Stem Cells and Acts in Lineage Choice and Leukaemia Prevention," Nature, 441, pp. 518-522 (2006).

Zhou et al., "Germline Mutations in BMPR1A/ALK3 Cause a Subset of Cases of Juvenile Polyposis Syndrome and of Cowden and Bannayan-Riley-Ruvalcaba Syndromes," Am. J. Hum. Genet., 69, pp. 704-711 (2001).

S. Saha and G.P.S Raghava, "Prediction of Continuous B-Cell Epitopes in an Antigen Using Recurrent Neural Network," Proteins: Structure, Function, and Bioinformatics, 65:40-48 (2006).

Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes," Journal of Virology, 75 (7):3277-3290 (2001).

Nilsen et al., "Monoclonal Antibodies against Human Immunodeficiency Virus Type 1 Integrase: Epitope Mapping and Differential Effects on Integrase Activities in Vitro," Journal of Virology, 70(3):1580-1587 (1996).

Banerjee et al., "Conformational and Linear B-Cell Epitopes of Asp f2, a Major Allergen of *Aspergillus fumigatus*, Bind Differently to Immunoglobulin E Antibody in the Sera of Allergic Bronchopulmonary Aspergillosis Patients," Infection and Immunity, 67(5):2284-2291 (1999).

El-Manzalawy et al., "Predicting Flexible Length Linear B-Cell Epitopes," Comput Syst Bioinformatics Conf., 7:121-132 (2008).

Lienhard, "Non-functional Phosphorylations?" Trends in Biochemical Sciences, 33(8):351-352 (2008).

* cited by examiner

SEQUENCE LISTING

<160> NUMBER OF SEQ ID NOS: 13

<210> SEQ ID NO 1
<211> LENGTH: 19
<212> TYPE: DNA
<213> ORGANISM: Artificial
<220> FEATURE:
<223> OTHER INFORMATION: Synthetic Construct

<400> SEQUENCE: 1
actcaaggca gggatgagc      19

```
<210> SEQ ID NO 2
<211> LENGTH: 20
<212> TYPE: DNA
<213> ORGANISM: Artificial
<220> FEATURE:
<223> OTHER INFORMATION: Synthetic Construct

<400> SEQUENCE: 2
aatctagggc ctcttgtgcc                                                 20

<210> SEQ ID NO 3
<211> LENGTH: 23
<212> TYPE: DNA
<213> ORGANISM: Artificial
<220> FEATURE:
<223> OTHER INFORMATION: Synthetic Construct

<400> SEQUENCE: 3
gcttgatatc gaattcctgc agc                                             23

<210> SEQ ID NO 4
<211> LENGTH: 15
<212> TYPE: PRT
<213> ORGANISM: Mus musculus

<400> SEQUENCE: 4

Gln Asp Thr Gln Arg Arg Thr Ser Met Gly Gly Thr Gln Gln Gln
1               5                   10                  15

<210> SEQ ID NO 5
<211> LENGTH: 13
<212> TYPE: PRT
<213> ORGANISM: Artificial
<220> FEATURE:
<223> OTHER INFORMATION: Synthetic Construct
<220> FEATURE:
<221> NAME/KEY: Xaa
<222> LOCATION: (1)..(1)
<223> OTHER INFORMATION: Cysteine or Absent

<400> SEQUENCE: 5

Xaa His Gln Asp Thr Gln Arg Arg Thr Ser Met Gly Gly
1               5                   10

<210> SEQ ID NO 6
<211> LENGTH: 781
<212> TYPE: PRT
<213> ORGANISM: Mus musculus

<400> SEQUENCE: 6

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Thr Ala Pro Ser Leu Ser Gly
            35                  40                  45

Lys Gly Asn Pro Glu Glu Glu Asp Val Asp Thr Ser Gln Val Leu Tyr
        50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
                100                 105                 110
```

```
Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
        130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
                180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
        210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
530                 535                 540
```

```
Gln Asp Thr Gln Arg Arg Thr Ser Met Gly Gly Thr Gln Gln Phe
545                 550                 555                 560

Val Glu Gly Val Arg Met Glu Ile Val Glu Gly Cys Thr Gly Ala
                565                 570                 575

Leu His Ile Leu Ala Arg Asp Val His Asn Arg Ile Val Ile Arg Gly
                580                 585                 590

Leu Asn Thr Ile Pro Leu Phe Val Gln Leu Leu Tyr Ser Pro Ile Glu
                595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
                660                 665                 670

Arg Leu Ser Val Glu Leu Thr Ser Ser Leu Phe Arg Thr Glu Pro Met
                675                 680                 685

Ala Trp Asn Glu Thr Ala Asp Leu Gly Leu Asp Ile Gly Ala Gln Gly
690                 695                 700

Glu Ala Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
                740                 745                 750

Leu Pro Asp Leu Gly His Ala Gln Asp Leu Met Asp Gly Leu Pro Pro
                755                 760                 765

Gly Asp Ser Asn Gln Leu Ala Trp Phe Asp Thr Asp Leu
    770                 775                 780

<210> SEQ ID NO 7
<211> LENGTH: 781
<212> TYPE: PRT
<213> ORGANISM: Homo sapiens

<400> SEQUENCE: 7

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
                20                  25                  30

Ser Gly Ile His Ser Gly Ala Thr Thr Thr Ala Pro Ser Leu Ser Gly
            35                  40                  45

Lys Gly Asn Pro Glu Glu Glu Asp Val Asp Thr Ser Gln Val Leu Tyr
50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
                100                 105                 110

Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
130                 135                 140
```

```
Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
            165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
            245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
            325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
            405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
            485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
            530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
```

```
                        565                 570                 575
Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780

<210> SEQ ID NO 8
<211> LENGTH: 22
<212> TYPE: DNA
<213> ORGANISM: Artificial
<220> FEATURE:
<223> OTHER INFORMATION: Synthetic Construct

<400> SEQUENCE: 8
ggactgtatg tggagcggtt tc                                                 22

<210> SEQ ID NO 9
<211> LENGTH: 21
<212> TYPE: DNA
<213> ORGANISM: Artificial
<220> FEATURE:
<223> OTHER INFORMATION: Synthetic Construct

<400> SEQUENCE: 9
ctggtaggag gccagcttct c                                                  21

<210> SEQ ID NO 10
<211> LENGTH: 23
<212> TYPE: DNA
<213> ORGANISM: Artificial
<220> FEATURE:
<223> OTHER INFORMATION: Synthetic Construct

<400> SEQUENCE: 10
agttcatttc caacccaccc tca                                                23

<210> SEQ ID NO 11
<211> LENGTH: 24
```

-continued

```
<212> TYPE: DNA
<213> ORGANISM: Artificial
<220> FEATURE:
<223> OTHER INFORMATION: Synthetic Construct

<400> SEQUENCE: 11
tctggaaaga aagtgcgttg tgcg                                              24

<210> SEQ ID NO 12
<211> LENGTH: 19
<212> TYPE: DNA
<213> ORGANISM: Artificial
<220> FEATURE:
<223> OTHER INFORMATION: Synthetic Construct

<400> SEQUENCE: 12
gaaggtgaag gtcggagtc                                                    19

<210> SEQ ID NO 13
<211> LENGTH: 20
<212> TYPE: DNA
<213> ORGANISM: Artificial
<220> FEATURE:
<223> OTHER INFORMATION: Synthetic Construct

<400> SEQUENCE: 13
gaagatggtg atgggatttc                                                   20
```

ANTIBODIES THAT BIND SPECIFICALLY TO PHOSPHORYLATED β-CATENIN

CROSS-REFERENCE TO RELATED APPLICATIONS

The present application claims benefit to U.S. provisional patent application No. 60/895,204 filed on Mar. 16, 2007, which is incorporated by reference in its entirety as if recited in full herein.

FEDERALLY SPONSORED RESEARCH OR DEVELOPMENT

This invention was made with government support under grant numbers P01DK53074 and DK070001 awarded by the National Institutes of Health. The government has certain rights in the invention.

FIELD OF INVENTION

The present invention relates to various molecules, including antibodies, that bind specifically to β-catenin phosphorylated at amino acid position Serine 552. Methods of making and using such molecules are also provided. Kits, including such molecules are further provided.

BACKGROUND OF INVENTION

The gastrointestinal (GI) system has a well-organized developmental architecture which includes intestinal stem cells (ISCs), transient amplifying (TA) progenitors, functionally mature cells, and apoptotic cells all of which are confined to identifiable regions in each crypt/villus unit. This developmental architecture forms a sequential array of compartments (or zones) which promote self-renewal of stem cells, proliferation of progenitors, differentiation of progenitors to mature cells, and apoptosis in the mature cells. The developmental architecture or microenvironment is generally divided into three functional compartments, based upon stages of stem cell development, including (1) self-renewal, (2) expansion or transient amplification, and (3) differentiation zones. These zones correspond to the developmental state of the ISCs.

The mucosa of the small intestine is involved in nutrient absorption and is characterized by evaginations into the villi, and at the bases of the villi, by short tubular invaginations into crypts. The villi are projections into the lumen and are covered predominantly with mature, absorptive enterocytes, along with occasional mucous-secreting goblet cells. At the base of the crypts are the ISCs, which continually divide and provide the source for all epithelial cells in the crypts and villi. ISCs are multipotent, undifferentiated cells that fundamentally retain the capacity for cell division and regeneration to replace various intestine cells that undergo apoptosis and die. They are thought to be located in the fourth or fifth position from the bottom of each crypt in the small intestine. ISCs are also found at the bottom of the table region of the villi of the large intestine. Recently crypt base columnar (CBC) located at the 0 position was shown to have stem cell properties. Unlike adult stem cells in other tissue systems, and for an unknown reason, the currently identified ISCs have a relatively high rate of cell proliferation. Consequently, ISCs provide a general system for studying stem cells and the regulatory mechanisms that govern their proliferation, growth, and differentiation. In particular, this system is suitable for examining tumor development and recurrence, as well as, evaluating cancer therapies.

It has been proposed that the failure of most current therapies to completely cure cancer is caused by "cancer stem cells," which are resistant to therapy aimed at destroying malignant proliferation. Recently, several lines of evidence demonstrated the existence of tumor-initiating cells in acute myeloid leukemia, breast cancer, and brain cancer. In these studies, cancer stem cells could be recognized by their ability to initiate tumors upon transplantation into a secondary host. Still, in vivo evidence, directly linking the mutated stem cells with initiation of neoplasms in the natural setting, is lacking. Further, these putative "cancer stem cells" have yet to be identified.

While there are many "causes" of intestinal cancer, it is well established that almost all cases begin with the development of benign polyps in the epithelial layer of the intestine. The epithelium of the small intestine is composed of a proliferation compartment (crypt) and a differentiation compartment in the villus region (FIG. 1A). Intestinal stem cells (ISCs), located at the 0, 4 or $5^{th}$ position from the crypt bottom and above Paneth cells, are the driving force for intestinal regeneration. ISCs give rise to daughter cells that undergo further proliferation in a transient-amplifying compartment (TAC), producing absorptive enterocytes and secretory lineages including goblet and enteroendocrine cells, as well as Paneth cells which are located at the crypt bottom. Several signal pathways are known to be involved in regulating this complex sequence of events. However, the molecular mechanisms controlling ISC numbers and the relationships between the signaling pathways that govern intestinal homeostasis are not completely understood.

Intestinal polyposis (IP) features a substantial increase in the number of crypts and a reduction in epithelial cell differentiation. A still unanswered question for IP, and for neoplasia in general, is whether stem cells are involved in polyp initiation. An increase in stem cell number has been proposed to be responsible for crypt expansion, but direct in vivo evidence for this proposal is still lacking.

Studies of human hereditary IP syndromes and equivalent animal models, which typically but not uniformly predispose affected individuals to GI cancers, have provided substantial insight into the genetic control of intestinal homeostasis, polyposis, and cancer. Polyposis can result from impaired bone morphogenetic protein (BMP) signaling, or by overactivation of Wnt/β-catenin signaling. Wnt/β-catenin signaling exert positive control on multiplication of both stem cells and crypts; whereas, BMP signaling restricts stem cell number and prevent polyposis in part by suppressing Wnt signaling.

Cowden disease (CD) (OMIM #158350) is a rare autosomal dominant disorder featuring multiple hamartomatous lesions including intestinal polyps. CD results from mutation in the tumor suppressor gene PTEN, which encodes a lipid and protein phosphatase that acts as a negative regulator of the phosphatidylinositol-3-OH kinase (PI(3)K)—Akt pathway. The roles of PTEN and Akt in intestinal homeostasis and polyposis have not been defined, but there is evidence that they could be key players in the interplay between Bmp and Wnt signals. Mutation of BMP receptor 1A can result in a Cowden-like syndrome resembling loss of PTEN. BMP signaling may in part be mediated by inhibition of PI3K/Akt activity via positive regulation of PTEN. In turn, PTEN inhibits while Akt enhances the nuclear localization of β-catenin. Likewise, the PI3K inhibitor Ly294002 can block nuclear localization of β-catenin and its transcriptional activity. It has been proposed that Akt assists Wnt signaling in promoting activation of β-catenin in ISCs. Akt can regulate β-catenin activity indirectly, through GSK3β, or directly, through phosphorylation of β-catenin which enhances β-catenin's nuclear function.

It is desired to develop compositions and methods for the induction of ISC self-renewal, proliferation, growth, and differentiation within the intestinal tissue architectural structure. Methods for controlling the molecular mechanisms that, in turn, control intestinal pathways are also desired. Identification of cell markers, including cell surface markers, that are useful for ascertaining the role of stem cells in crypt expansion are desired. It is especially desired to identify distinct markers, which can be used to identify various types of cells such as "cancer stem cells" in the tissue.

SUMMARY OF INVENTION

Herein, is provided a novel system to examine the role of the PTEN/Akt pathway in the intestine directly through a mouse model in which PTEN is conditionally inactivated using a polyinosine-polycytidine (pIpC) inducible Mx1-Cre system and in which gene deletion can be targeted effectively in intestinal epithelial cells including stem cells. The inventors found that deleting PTEN from the intestine results in intestinal polyposis (IP) characterized by an increase in crypt number. Loss of PTEN results in excess ISCs/progenitors which initiate new crypt formation, implicating mutant stem cells in the origins of neoplasia. PTEN is expressed in the TAC, in ISCs, and in progenitors expressing ISC-like markers, and acts as a negative cell cycle regulator in these cell populations. Herein, results show that Akt directly phosphorylates β-catenin at $Ser^{552}$, generating a C-terminal phosphorylated form that is present in the nucleus of ISCs/progenitors, thereby establishing a molecular mechanism linking the bone morphogenic protein (BMP), PTEN/Akt and Wnt/β-catenin pathways in intestinal homeostasis.

The present invention relates to compositions and methods which can be used to influence proliferation, self-renewal, cell differentiation, and apoptosis in intestinal cells and tissue, both in vivo and in vitro. The methods and compositions can be utilized in the disclosed mouse model, isolated cells, isolated tissue cultures, or in vivo in other organisms, such as in a rat or other mammal. This information can be used to create models, kits, and cultures useful in studying and treating intestinal polyposis, as well as Cowden's disease, in humans. Further, the compositions and methods can also be used in conjunction with procedures for screening putative anti-tumor therapies or anti-inflammatory drugs.

The invention provides a conditional mutant $Mx1-Cre^+$ $PTEN^{fl/fl}$ mouse model in which application of a recombination activator results in the loss of expression of functional PTEN polypeptide in at least one intestinal cell. The intestinal cell may be an intestinal epithelial, intestinal stem, transient amplifying progenitor, mucosal progenitor, columnar progenitor, enterocyte, mesenchymal, Paneth, goblet, or enteroendocrine cell. Further, a conditional mutant $Mx1-Cre^+$ $PTEN^{fl/fl}$ mouse, such as a $Mx1-Cre^+PTEN^{fl/fl}$ Z/EG mouse is provided.

The loss of expression of functional PTEN can occur through a number of means, any of which are suitable in the practice of the invention. For example, mutant intestinal cells may comprise a nonfunctional mutant PTEN gene, wherein the mutant PTEN gene encodes an inactive or truncated PTEN protein or polypeptide. Alternatively, the PTEN gene may be mutated such that all expression of PTEN is essentially eliminated.

Preferred recombination activators are interferon and pIpC; however, the skilled artisan will recognize that other activators may be used as the origin of the recombination activator is not believed to be particularly crucial to the practice of the invention.

An intestinal cell that is successfully mutated to lose expression of functional PTEN can be phenotypically identified by the mutated cell's increased expression of phosphorylated β-catenin (p-β-catenin). Mutated intestinal cells express two-fold or more greater phosphorylated nuclear β-catenin compared to nonmutant intestinal cells. Preferably, the nuclear β-catenin is phosphorylated at any one amino acid within the Armadillo repeat R10 of β-catenin, S552 (Ser552), T217, T332, or S675. Most preferably, the nuclear β-catenin is phosphorylated at Ser552.

The $Mx1-Cre^+PTEN^{fl/fl}$ knock-out mouse may also be identified phenotypically by expanded ISC numbers, intestinal polyps, and intestinal tumor phenotypes.

Prior to recombination, the pre-excision $PTEN^{fl/fl}$ knock-out mutant mouse will include an intestinal cell having a recombination site-flanked PTEN gene. Those of skill in the art will recognize that several recombination systems are available in the art. It is believed that the system that is chosen is not particularly crucial to the practice of the invention, so long as the expression of functional PTEN polypeptide is essentially eliminated and nuclear β-catenin levels are altered by at least two-fold in mutant intestinal cells compared to control or wild type intestinal cells such that the described mutant phenotypes occur.

An exemplary recombination system that is preferred by the inventors is a Cre/lox recombination system. Such a recombination system is described, e.g., in U.S. Pat. No. 4,959,317, which is incorporated by reference as if recited in full herein.

The invention also provides a method for making a mouse model of Cowden disease comprising forming a pre-excision PTEN mutant Mx1-Cre-Lox mouse pup; and administering a recombination activator to excise a PTEN gene to form a post-excision PTEN mutant Mx1-Cre-Lox mouse pup, wherein the PTEN protein is inactivated, and an intestinal cell of the post excision PTEN mutant Mx1-Cre-Lox pup expresses two-fold or more greater phosphorylated nuclear β-catenin compared to a nonmutant intestinal cell. This mouse model is useful for detecting a phenotypic change in murine intestinal tissue such as the occurrence of polyposis, increased crypt formation, increased cell proliferation, abnormal differentiation, and increased expression of phosphorylated nuclear β-catenin. The murine tissue will comprise at least one mutated goblet, Paneth, mucin-producing, enterocyte, tumorous, or polyp cell. Most preferably, the intestinal tissue will comprise a mutated intestinal stem cell.

Another method of practicing the invention provides for detecting mutant PTEN/Akt pathway signaling that is associated with polyposis in an intestinal cell of an intestinal cell population. The method comprises immunizing an animal with a marker selected from the group consisting of phosphorylated β-catenin, wherein phosphorylation occurs at least at one position selected from the group consisting of S552, T217, T332, S675, and any amino acid of the Armadillo repeat R10 of β-catenin; isolating the marker antibody, wherein the marker antibody binds to the marker; attaching a label to the isolated marker antibody to form a labeled anti-marker antibody; administering the labeled anti-marker antibody to a target cell of the intestinal cell population; wherein the labeled anti-marker antibody binds to the marker in the target cell; and detecting the presence of the labeled anti-marker antibody in the target cell, wherein the labeled antibody identifies the presence of the marker polypeptide in the target cell.

In another embodiment of the invention, a purified antibody is provided. The antibody binds specifically to β-catenin phosphorylated at amino acid position Serine$^{552}$.

In a further embodiment of the invention, a purified molecule is provided. This purified molecule binds specifically to β-catenin phosphorylated at amino acid position Serine$^{552}$.

A further embodiment of the invention is a purified antibody that binds to a polypeptide consisting of SEQ ID NO:4 or SEQ ID NO:5.

In another embodiment, the invention is an antibody deposited with ATCC under accession number PTA-9077.

A further embodiment of the invention is a method of making an antibody. This method comprises immunizing a non-human animal with an immunogenic fragment from an Armadillo domain of β-catenin that is phosphorylated by Akt.

Another embodiment of the invention is a method of detecting a phosphorylation state of β-catenin. This method comprises determining whether Serine$^{552}$ of β-catenin is phosphorylated.

A further embodiment of the invention is a kit for detecting phosphorylation at Serine$^{552}$ of β-catenin. This kit comprises a purified antibody that binds specifically to β-catenin phosphorylated at amino acid position Serine$^{552}$ and instructions on how to use the antibody.

In another embodiment, the invention provides a kit for detecting mutant PTEN/Akt pathway signaling associated with polyposis in an intestinal cell of an intestinal cell population, wherein the kit comprises a container; and an anti-p-β-catenin antibody attached to a label, wherein the anti-p-β-catenin antibody specifically binds to a phosphorylated β-catenin, wherein phosphorylation occurs at least at one position selected from the group consisting of S552, T217, T332, S675, and any amino acid of the Armadillo repeat R10 of β-catenin, and the anti-p-β-catenin antibody does not specifically bind to a β-catenin not phosphorylated at least at one position selected from the group consisting of S552, T217, T332, S675, and any amino acid of the Armadillo repeat R10 of β-catenin.

Such kits may include more than one antibody. For example, the kit may include an anti-p-β-catenin antibody attached to a label, wherein the anti-p-β-catenin antibody specifically binds to a nuclear β-catenin phosphorylated at position $S^{552}$; and a second anti-p-β-catenin antibody attached to a label, wherein the second anti-p-β-catenin antibody specifically binds to a phosphorylated β-catenin, wherein phosphorylation occurs at least at one position selected from the group consisting of S552, T217, T332, S675, and any amino acid of the Armadillo repeat R10 of β-catenin, and the second anti-p-β-catenin antibody does not specifically bind to a β-catenin not phosphorylated at least at one position selected from the group consisting of S552, T217, T332, S675, and any amino acid of the Armadillo repeat R10 of β-catenin. Such kits may be useful, e.g., in the further study of the PTEN/Akt pathway and the identification of intestinal stem cells that give rise to polyps and neoplasia.

The kits of the present invention may include one or more labels such as fluorescent, phosphorescent, luminescent, radioactive, and chromogenic labels. The choice of label is not believed to be crucial to the practice of the invention, as long as the antibodies or anti-markers are able to specifically recognize their intended antigen, i.e. phosphorylated β-catenin.

BRIEF DESCRIPTION OF DRAWINGS

The application file contains at least one drawing executed in color. Copies of this patent application publication or any patent to issue therefrom with color drawing(s) will be provided by the Office upon request and payment of the necessary fee. The following drawings form part of the present specification and are included to further demonstrate certain aspects of the present invention. The invention may be better understood by reference to one or more of these drawings in combination with the detailed description of specific embodiments presented herein.

FIG. 1A diagrams the intestinal structure composed of crypt and villus regions in which intestinal stem cells, proliferating progenitor cells, and differentiated cells are located in spatially defined compartments. FIGS. 1B-1E show determination of expression of Cre and targeting efficiency in crypt cells including ISC (Musashi+ cells) (FIG. 1B) using the compound genetic mouse model Mx1-Cre$^+$; Pten$^{fl/fl}$; ZEG. Green signal is present where Cre activity has deleted the Pten gene and activated GFP in the reporter. Days post pIpC induction are shown in parentheses. One month after induction, multiple intestinal polyps formed in the PTEN mutant animals (FIG. 1F), as confirmed by histological staining of a polyp from a Pten mutant mouse at one month post pIpC injection (FIG. 1G). PCR confirmed successful targeting of the PTEN gene. Lane 1—homozygote with both Pten alleles flanked by LoxP sites; Lane 2—Wt line; Lane 3—heterozygote; Lane 4—efficient deletion of exon5 (ex5) in the Pten locus (FIG. 1H). Proliferation zones, as measured by 3-hour BrdU-pulse labeling, were compared in the intestines of control and Pten mutant mice (FIGS. 1I-1K) and their proliferation indices were compared (FIG. 1L).

FIG. 2D shows results of Western blot analysis that indicates increased levels of p-Akt and p-GSK3β (upper panel), and Cyclin D1 (lower panel), as well as, results of an RT-PCR assay showing increased levels of Myc and Cyclin D1 (mid panel) in the Pten mutant intestine. FIG. 2E summarizes microassay results that show changes in cell cycle-related genes in the PTEN mutant mouse. Red/green colors indicate signal level for a sample relative to the average for all five samples. * indicates genes identified with the BioCarta term "Cell cycle: G1/S check point".

FIG. 3E shows a three-dimension photo showing crypt fission in the PTEN mutant intestine. Musashi1+ intestinal stem cells/progenitor cells (M$^+$ISC/p) are detected in the apex of bifurcated fission crypts (FIGS. 3F and 3G). FIG. 3H is a schematic showing the relationship between M$^+$ISC/p (red) and crypt fission. FIG. 3I is a three-dimension photo of crypt budding in the PTEN mutant intestine. In FIGS. 3J-3K, M+ISC/p are found at the point of initiation of crypt budding or de novo crypt formation. The white arrows in FIG. 3J and FIG. 3K, respectively, indicate a cluster of M+ISC/p cells detected in a region undergoing invagination (a process that usually occurs only in the fetal stage) (FIG. 3J) and budding (FIG. 3K). The selected window shown in FIG. 3J represents the newly formed crypt (FIG. 3K). FIG. 3L is a graph showing increased percentage of crypt fission and budding in the PTEN mutants. FIGS. 3M-3N show increase in M+ISC/p in the polyp region (FIG. 3M) and duplicate M+ISC/p in the newly formed crypt (FIG. 3N). The majority of M+ISC/p cells in the polyp region are Ki67$^{-ve}$ (FIG. 3N). FIG. 3O is a model showing the involvement M+ISC/p (red) in de novo crypt formation in the PTEN mutant polyp region.

FIGS. 4A-4D show ISC expression of Musashi1, components of the PTEN-Akt pathway, and nuclear Cyclin D1 in control cells. Musashi1 is co-localized with 14-3-3ζ (FIG. 4A). 14-3-3ζ is co-localized with p-PTEN (FIG. 4B). PTEN-Akt signaling in ISCs is associated with nuclear or nuclear plus cytoplasmic p27$^{kip1}$ (FIG. 4C) and nuclear Cyclin D1 (FIG. 4D). FIGS. 4E-4J shows that the number of p-Akt+ (FIGS. 4E-4G) and p-GSK3β-S$^{9+}$ (FIGS. 4H-4J) cells is increased in the polyp regions of the Pten mutant mice (FIGS. 4F, 4G, 4I, 4J) when compared to intestine from control mice (FIGS. 4E, 4H). Red arrows indicate strongly positive cells. (FIGS. 4F, 4G) and (FIGS. 4I, 4J) are adjacent sections from the same polyp. Control sections illustrate cells at the ISC position strongly positive for p-Akt (FIG. 4E) and p-GSK3β-S$^9$ (FIG. 4H). Some additional strongly positive cells are also observed in the middle or upper regions of the crypt (see FIG. 8). FIGS. 4K-4M illustrate detection of cells with β-catenin transcriptional activity, which was mainly detected in cells at stem and Paneth cell positions in control mice but was detected in multiple places including the villus region in the PTEN mutant mice, with Top-Gal. The number of cells with nuclear Cyclin D1 is increased in the polyp region of Pten mutant mice (FIGS. 4O, 4P) compared to control (FIG. 4N). The number of cells with nuclear p27$^{kip1}$ (red arrows) is increased in the polyp region of PTEN mutants (FIGS. 4R-4S) compared with control intestine (FIG. 4Q). FIG. 4T shows a western blot comparison of the level and phosphorylation state of p27kip1 in control and PTEN mutant intestines. FIG. 4U shows a schematic illustration of the PTEN-Akt signaling pathway that assists Wnt to control β-catenin activity. FIG. 4V shows a schematic illustration of the PTEN-Akt signaling pathway that controls cell cycle entry and progression.

FIG. 5A shows Scansite® 2.0 output identifying S$^{552}$ as a putative Akt phosphorylation site (basophilic serine/threonine kinase site) towards the C-terminus of β-catenin. The site is located in the 10th of the 12 Armadillo (Arm) repeats and has high accessibility. FIG. 5B shows mass-spectrometry analysis identified a phosphorylated peptide generated by incubation of a murine β-catenin protein with activated Akt. A high intensity peak corresponding to loss of 98 Da (−98) is indicative of phosphorylation. Additional peaks correspond to the b- and y-ions expected for the peptide shown in FIG. 5C. FIG. 5C shows the amino acid sequence of the murine β-catenin peptide identified as containing an Akt phosphorylation site, showing the masses of the expected b- and y-ions. The * marks the phosphorylated serine$^{552}$. FIG. 5D shows results of Western blotting using anti-β-catenin (NT-nP) that confirm that anti-p-beta-cat-Ser552 antibody recognizes the active form of β-catenin. The anti-p-beta-cat-Ser552 antibody, which is a rabbit polyclonal antibody against murine β-catenin phosphorylated at amino acid position S552 identifies an 88-kd band, which corresponds to the murine β-catenin. Crypt proteins were immunoprecipitated using anti-p-beta-cat-Ser552 antibody (or IgG as a control). Inset: the purified crypts used for the assay. FIG. 5E shows western blot determination of the phospho-specificity of anti-p-beta-cat-Ser552 antibody by use of non-phosphorylated (Np) or phosphorylated (p) peptide blocking. Levels of anti-p-beta-cat-Ser552 antibody in PTEN mutant polyps are increased compared with control intestine.

FIGS. 6D-6G show the distribution pattern of β-catenin in crypts as detected by anti-NT-np (N-terminal non-p form) (FIG. 6D and FIG. 6F) and anti-p-beta-cat-Ser552 antibody (FIG. 6E and FIG. 6G). Red arrows indicate ISC position (FIGS. 6D-6E) and dividing ISCs (FIGS. 6F-6G). MC=mesenchymal cell. In FIGS. 6I-6K active Akt and nuclear β-cat-p-S$^{552}$ (brown) correlates with Top-Gal activity (blue) in some crypt cells including ISCs. Cont.: Mx1-Cre+PTEN$^{fl/+}$, PTEN Mut.: Mx1-Cre+PTEN$^{fl/fl}$. FIGS. 6L-6M illustrate regulation of nuclear β-catenin by Wnt and Akt pathways suggesting a relationship between phosphorylation and nuclear activity of β-catenin. Nuclear-localized forms of β-catenin are identified by N-terminal non-phosphorylation, by C terminal phosphorylation at S$^{552}$, or both.

FIGS. 7D and 7E are serial views of dividing crypts (fission) (FIG. 7D) and budding crypts (FIG. 7E) in PTEN mutants obtained by whole-mount immuno-fluorescence and confocal microscopy. Cells with nuclear β-cat-p-S$^{552}$ were found at the initiation sites of fission or budding crypts. Cryptdin was used to reveal the Paneth cells.

FIGS. 9A and 9B provide examples of crypt fission in Musashi+ cells as seen in the apex of bifurcating crypts (bottom-up model). FIGS. 9C-9E illustrate de novo crypt formation (top-down model). A cluster of Musashi+ cells were detected at the transition zone between crypt and villus (FIG. 9C), unlike normal intestine in which a single Musashi+ cell was occasionally detected at this location. Red arrows indicate sites that may initiate invagination (compare to FIG. 9E). FIGS. 9D-9E illustrate crypt budding from an existing crypt in which Musashi+ cells are at the initiation point (FIG. 9E, red arrows). FIG. 9F shows a cluster of Musashi+ cells that were detected in the villus region in the PTEN mutant intestines. FIG. 9G illustrates sequential formation of new crypts in which Musashi+ cells are located at the initiation site of new crypts (red arrows). A cartoon of this model is shown in FIG. 9H.

FIGS. 10A-10B show examination of Musashi1 expression in a section of control intestine. Musashi+ cells were mainly located in crypts. The expression pattern of Musashi1 detected by 14H1 antibody is broader than that detected by the antibody provided by Chemicon (AB5977). FIGS. 10C-10E show examination of Musashi1 expression in a section of the PTEN mutant intestine. A Musashi+ cell cluster can be seen in the villus region (FIGS. 10D, 10E), which is similar to that detected by antibody AB5977.

FIG. 11A shows that cells with nuclear β-catenin detected by anti-p-beta-cat-Ser552 antibody were found in positions located between villus and crypt (far left panel), stem cell, Paneth cells (left panel), and mid-upper region of crypts (right panel). Perinuclear β-catenin at relatively low levels was found in some crypt cells of PTEN mutant animals (far right panel). FIG. 11B shows that cells positive for Top-Gal were found mainly in crypts, in which Top-Gal-positive cells were seen in cells at the stem cell position (far left panel), Paneth cells (right panel), and the mid-upper regions of crypts (left panel). In the early stage of PTEN mutant intestine, clusters of Top-Gal-positive cells were also seen in the villus region (far right panel). FIG. 11C shows that cells with nuclear $p27^{kip1}$ were mainly found in the stem cell position (left panel) and Paneth cells (middle panel), and correlated with pAkt. Cells with cytoplasmic $p27^{kip1}$ were often found in the mid-upper region of crypts and also correlated with high levels of p-Akt (right panel). FIG. 11D shows that cells with nuclear cyclin D1 were mainly found in the stem cell position, in Paneth cells, and the mid-upper regions of crypts. FIG. 11E shows staining of $p27^{kip1}$ alone (right panel) or co-stained with Musashi (far left panel), β-catenin (left panel), and β-catenin-$S^{552}$ (far right panel).

FIGS. 12A-12B show a comparison of distribution patterns of cells with nuclear β-cat-p-$S^{552}$ between control (FIG. 12A) and PTEN mutant (FIG. 12B) cells. FIG. 12C shows a magnified selected region in a polyp from FIG. 12B that shows fission crypts. FIG. 12C also shows multiple crypt cells with lower levels of perinuclear β-cat-p-$S^{552}$ (black arrows), as well as, cells exhibiting higher levels of perinuclear β-cat-p-$S^{552}$ (red arrows). FIG. 12D shows a quantification of the number of cells with high levels (red arrow) of nuclear β-cat-p$S^{552}$ in equal lengths (5 crypt distance) of intestine.

DETAILED DESCRIPTION

Figure 1:
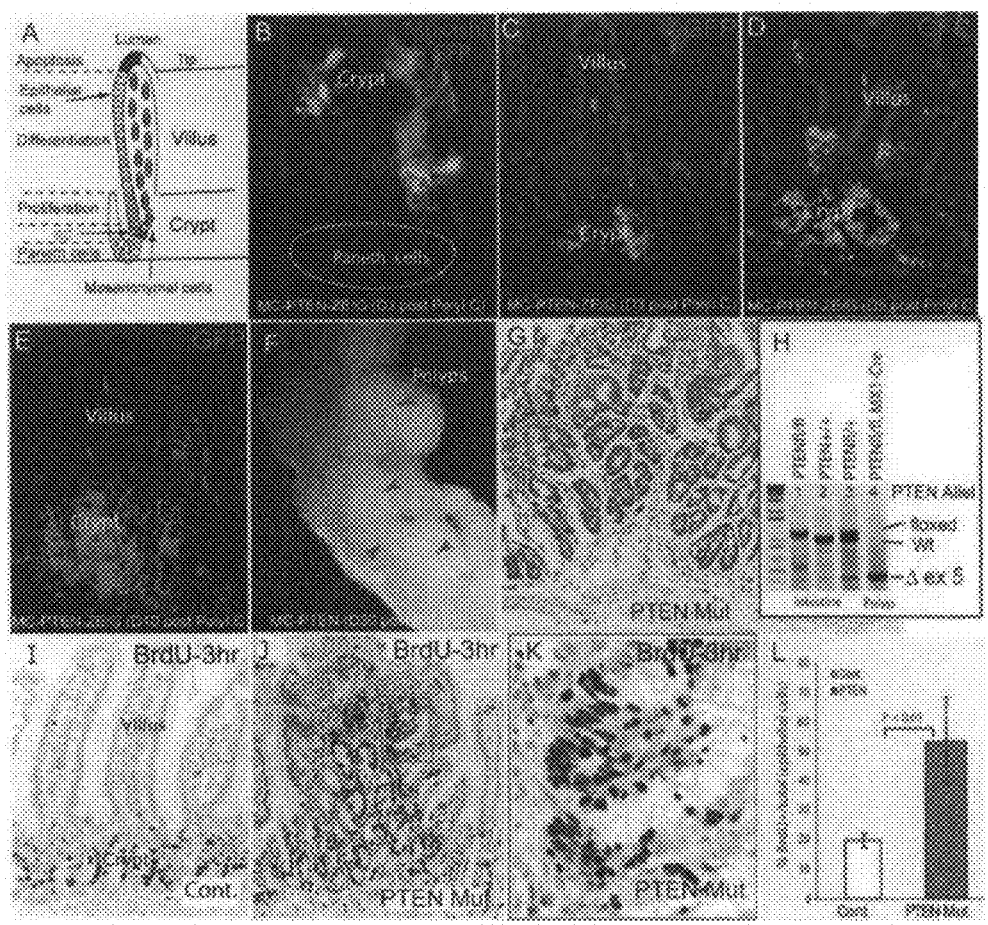
FIG. 1 illustrates that inactivation of PTEN leads to intestinal polyposis.

Using a conditional knock-out mouse model, the inventors show that the tumor suppressor Phosphatase of Tension homolog (PTEN) governs the proliferation rate and number of ISCs and that loss of PTEN results in an excess of ISCs. In PTEN mutants, the excess ISCs initiate both de-novo crypt formation and crypt fission, recapitulating crypt production in the fetal/neonatal intestine. The PTEN/Akt pathway likely governs stem cell activation by helping control nuclear localization of the Wnt effector β-catenin. Akt phosphorylates β-catenin at $Serine^{552}$, resulting in a form that is nuclear localized in ISCs. Taken together, these observations show that intestinal polyposis is initiated by PTEN mutant stem cells that undergo excessive proliferation driven by Akt activation and nuclear localization of β-catenin.

I. Two Roles For PTEN In Intestinal Polyposis

Until now, in vivo evidence to directly link mutated stem cells with initiation of neoplasia in the natural setting has been lacking. Herein, is shown that, in the intestine, PTEN acts as a negative regulator of cell cycling, performing this function both in the TAC and in ISCs/progenitors. The roles of PTEN in the homeostasis of these two cell populations are reflected in how its loss contributes to intestinal polyposis. PTEN-deficient polyps are more proliferative than normal intestine because PTEN normally helps limit the proliferation of a sub-population of the TAC. PTEN also governs the proliferation rate, and therefore the number, of M+ISC/p. PTEN loss leads to an excess of ISCs/progenitors. Evidence provided herein demonstrates that the excess stem cells seed the production of polyps through crypt fission or budding, thus providing a direct link between abnormal ISC production and the initiating centers of neoplasia in crypt multiplication and IP. In other words, the methods and compositions, including the conditional mouse model and specific antibody of the invention provide the means with which to directly identify "cancer stem cells".

A. PTEN Controls Cell Cycle in the Transit-Amplifying Compartment

In the normal TAC, non-p-PTEN expressed by the non-actively cycling sub-population of cells actively inhibits PI(3) K/Akt and restrains cellular proliferation. The increased proportion of cells in S phase in PTEN mutant polyps and the global changes in mRNA/protein expression are consistent with Akt promoting cell cycle entry, G1 progression and/or G1/S transition. Data herein suggest that there are two important effectors of PTEN/Akt control of intestinal proliferation: (1) Akt targeting of Myc, which promotes G1 transition, and (2) Cyclin D1, which is synthesized in early G1 and is required for transition to S.

B. ISC/Progenitor Over-Production and the Initiation of Intestinal Polyposis

PTEN loss results in an increased number and altered distribution of the M+ISC/p cell population. Stem cells are relatively long-lived and can accumulate over time in PTEN mutants as a result of their increased proliferation. At this stage, however, the possibility that PTEN-deficient ISC/progenitors might more frequently undergo symmetric division to generate additional ISC/progenitors cannot be excluded. But, as Akt governs cell migration, the proposal that PTEN controls the adhesion, migration or niche interaction properties of M+ISC/p has good support. It is possible, however, that dispersal and clustering of M+ISC/p are more passive processes, reflecting dynamic forces exerted on them by the aberrant division/migration of their non-stem cell daughters. Aberrantly localized M+ISC/p might also be generated if descendents of PTEN-deficient ISCs that would normally lose ISC properties retain or re-acquire these properties, a process that may require a secondary mutation. Overall, the enhanced proliferation and altered distribution of PTEN-deficient ISCs resembles the behavior of PTEN-deficient hematopoietic stem cells, which cycle more actively than normal and are impaired in their ability to lodge in bone marrow niches. The data herein support the conclusion that negative regulation of cell cycle is a common action of PTEN in stem cell populations and may in some cases be coupled with control of stem cell location.

There is a striking association between ISCs/progenitors and the sites where new crypts form, which suggests that this cell population is responsible for the genesis of crypts, making stem cells central to the initiation of polyposis. Both crypt fission, a 'bottom up' mechanism of polyp formation, and crypt budding, 'a top down' mechanism, feature M⁺ISC/p cells at the initiation site. Crypt fission, a component of normal intestinal growth and repair as well as a feature of polyposis, has been suggested to occur when the number of ISCs in a crypt exceeds some threshold capacity and the data herein validate this concept. Similarly, it is proposed that aberrantly placed Musashi⁺ cells direct the de-novo budding morphogenesis of crypt-like structures from existing villi or crypts. This budding process will likely share some of the molecular and cellular characteristics of the initial formation of crypts during intestinal development where Musashi⁺ cells exhibit a similar distribution.

II. Co-Operative Action of the Wnt and PTEN-Akt Pathways in ISC Activation

The nuclear localization of β-catenin is considered a critical event in stem cell activation and therefore for homeostasis of the intestine. The highly restricted pattern of nuclear β-catenin in the intestine is somewhat puzzling since many Wnt-pathway components are expressed rather broadly or in gradients and the widespread distribution of the phosphorylated form of Wnt co-receptor LRP6 suggests that all proliferating cells in crypts are exposed to Wnt signaling. It is proposed that Akt can assist the Wnt pathway to regulate nuclear localization of β-catenin: Akt activity is localized to the same population of ISC/progenitors as nuclear β-catenin and could thus provide the necessary spatial specificity. Herein, the inventors now identify the molecular link between β-catenin nuclear localization and the activity of the PTEN/Akt pathway. Akt phosphorylates β-catenin at $Ser^{552}$ and the resulting β-cat-p-$S^{552}$ form has a nuclear distribution. Loss of PTEN results in an increase in the number of ISC/progenitors with nuclear β-catenin as well as higher levels of nuclear β-cat-p-$S^{552}$. Moreover, ISCs/progenitors participating in crypt fission and crypt budding have nuclear β-cat-p-$S^{552}$.

Precisely how phosphorylation of $Ser^{552}$ influences the nuclear localization of β-catenin remains to be determined, but the location of the Akt target site suggests possible mechanisms. The central region of β-catenin consists of twelve triple helical Armadillo repeats (R1-R12) that form a long superhelical structure and $Ser^{552}$ is located near the start of the 22 amino acid insertion which interrupts R10. The R10 to C-terminal region, and R10 itself, is implicated in the nuclear import and export of β-catenin, so phosphorylation of $Ser^{552}$ and other sites could modulate translocation through nuclear pores. Equally, phosphorylation-dependant conformation changes in β-catenin are known, and $Ser^{552}$ lies in the region of a proposed conformational change that helps partition β-catenin between nuclear and membrane pools. In explaining the nuclear distribution of β-cat-p-$S^{552}$ in M⁺ISC/p it is important to recognize that phosphorylation at this site is unlikely to be the sole or even primary determinant of localization, which probably requires additional modifications elsewhere in β-catenin. Akt commonly phosphorylates more than one site within its target molecule and may be expected to also phosphorylate one or more of T217, T332 and S675. Both S552 and S675 have recently been reported to be phosphorylated by the PKA, which raises confidence these are authentic serine-threonine kinase phosphorylation sites. In that PKA study, however, assays performed in Cos7 cells suggested that neither of the S552 and S675 phosphorylation sites greatly affects β-catenin nuclear localization, although they may influence its transcriptional activity. Thus, further studies are required to define the mechanism underlying nuclear localization of p-β-cat-$S^{552}$ in M⁺ISC/p and elucidate the role that Akt and specific Akt target sites play in β-catenin nuclear localization and function in vivo.

III. Molecular Control of ISC/Progenitor Proliferation by the PTEN/Akt Pathway

M⁺ISC/p are a slow-cycling cell population. They are rarely Ki67⁺ and it appears likely that most are normally quiescent or arrested (in G0 or G1), with a significant proportion exhibiting nuclear localized β-catenin, Cyclin D1, and $p27^{kip1}$, a typical signature of the G1 phase. Although M⁺ISC/p are slow-cycling many contain phosphorylated forms of PTEN, Akt and the Akt target GSK3β (p-PTEN, p-Akt, p-GSK3β), which are consistent with an active Akt pathway. To reconcile this finding, it is proposed that Akt is an important component of the activation of ISCs/progenitors, but further signals appear to be required for ISCs in G1 to undergo a G1-S transition. The ISCs/progenitors that actively cycle are a small proportion of a rare cell type within the intestine, and they cannot yet be prospectively sorted, which limits the ability to fully assess the molecular changes that occur in this population when PTEN is deleted. Nevertheless, loss of PTEN markedly increases the proportion of ISCs/progenitors that are more actively cycling and also increases the number of ISCs/progenitor cells with p-Akt, p-GSK3β, nuclear p-β-cat-$S^{552}$, nuclear Cyclin D1 and nuclear $p27^{kip1}$, as well as, increasing the levels of $T^{157}$-phosphorylated $p27^{kip1}$. Thus, it is proposed that PTEN/Akt pathway governs ISC/progenitor proliferation and number by co-operating with the Wnt pathway to control nuclear localization of β-catenin, and hence the regulation of β-catenin targets such as Cyclin D1. In addition, Akt phosphorylation of $p27^{kip1}$ may also be involved in promoting G1/S transition.

Developing therapies that can target cancer stem cells but not normal stem cells requires better knowledge of the properties of both. Data herein show that loss of PTEN causes M⁺ISC/p to cycle more rapidly. The involvement of this population in the initiation of crypt budding and crypt fission in IP was characterized, and the mechanism by which the PTEN/Akt and Wnt pathways are directly coupled in stem cells was determined. It is proposed that a pathway by which PTEN/Akt may regulate stem cell proliferation and number exists and suggested that PTEN/Akt also controls the localization of ISC/s progenitors. Together these findings provide better understanding of how stem cell behavior is controlled and how mutant stem cells contribute to neoplasia.

IV. A Mouse Model Of Hamartomatous Polyposis And Cowden Disease

In Cowden disease, which results from human PTEN mutations, multiple hamartomatous lesions develop and feature contributions from both epithelial and stromal cells. Interferon (or pIpC)-mediated PTEN deletion in the mouse model described herein accurately recapitulates the hamartomatous intestinal polyposis evident in human CD, producing a valuable animal model of this disorder, for intestinal polyposis in general, and for intestinal inflammation. The altered proliferation of M⁺/ISP and TAC observed in the mutants strongly correlate with PTEN expression and with the Akt pathway activity within the intestinal epithelium, consistent with a local requirement for PTEN, but the stromal contribution to hamartomatous polyposis remains to be determined. Use of the Mx1-Cre PTEN model of CD, together with alternative forms of PTEN deletion, will help dissect the complex phenotype further, and may provide a novel platform in which to explore key issues in gastrointestinal disease, such as interaction between intestinal injury or inflammation and the initiation or progression of neoplasia.

It is envisioned that this Mx1-Cre PTEN model will also be useful for the screening of possible therapeutic agents for treating CD, IP, neoplasia, and other gastrointestinal disease in which the proposed PTEN and Akt interactions are necessary to either the development or progression of the disease. For example, the Mx1-Cre PTEN model may be used to assess the ability of proposed therapeutics to reverse or reduce the occurrence of polyps or inflammation. Alternatively, alternative forms of PTEN deletion may be assessed to further characterize the distinctions between various forms of IP such that further target sites for putative therapeutics may be identified.

Such screening assays will preferably follow the standard protocols used to administer putative therapeutic compounds then follow the methodology provided in the Examples herein to detect altered regulation, i.e., a change of two-fold or greater in the up or down regulation using microassay analysis as provided, e.g., in the Examples below, of nuclear β-catenin and ISCs.

Antibodies

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody. These and other antibodies are disclosed in U.S. Published Patent Application No: 20070065447.

A. Polyclonal Antibodies

Means for preparing and characterizing antibodies are well known in the art (see, e.g., Antibodies: A Laboratory Manual, Cold Spring Harbor Laboratory, 1988; incorporated herein by reference). To prepare polyclonal antisera, an animal is immunized with an immunogenic p-β-catenin composition, and antisera collected from that immunized animal. The immunologic p-β-catenin composition, e.g., a β-cat-p-$S^{552}$-containing epitope, may be obtained from any species, particularly a mammalian species, including rodents and primates, such as, e.g., murine or human.

A wide range of animal species can be used for the production of antisera. Typically, the animal used for production of anti-serum is a rabbit, mouse, rat, hamster, guinea pig, or goat. Because of the relatively large blood volume of rabbits, a rabbit is generally a preferred choice for production of polyclonal antibodies.

Figure 13:
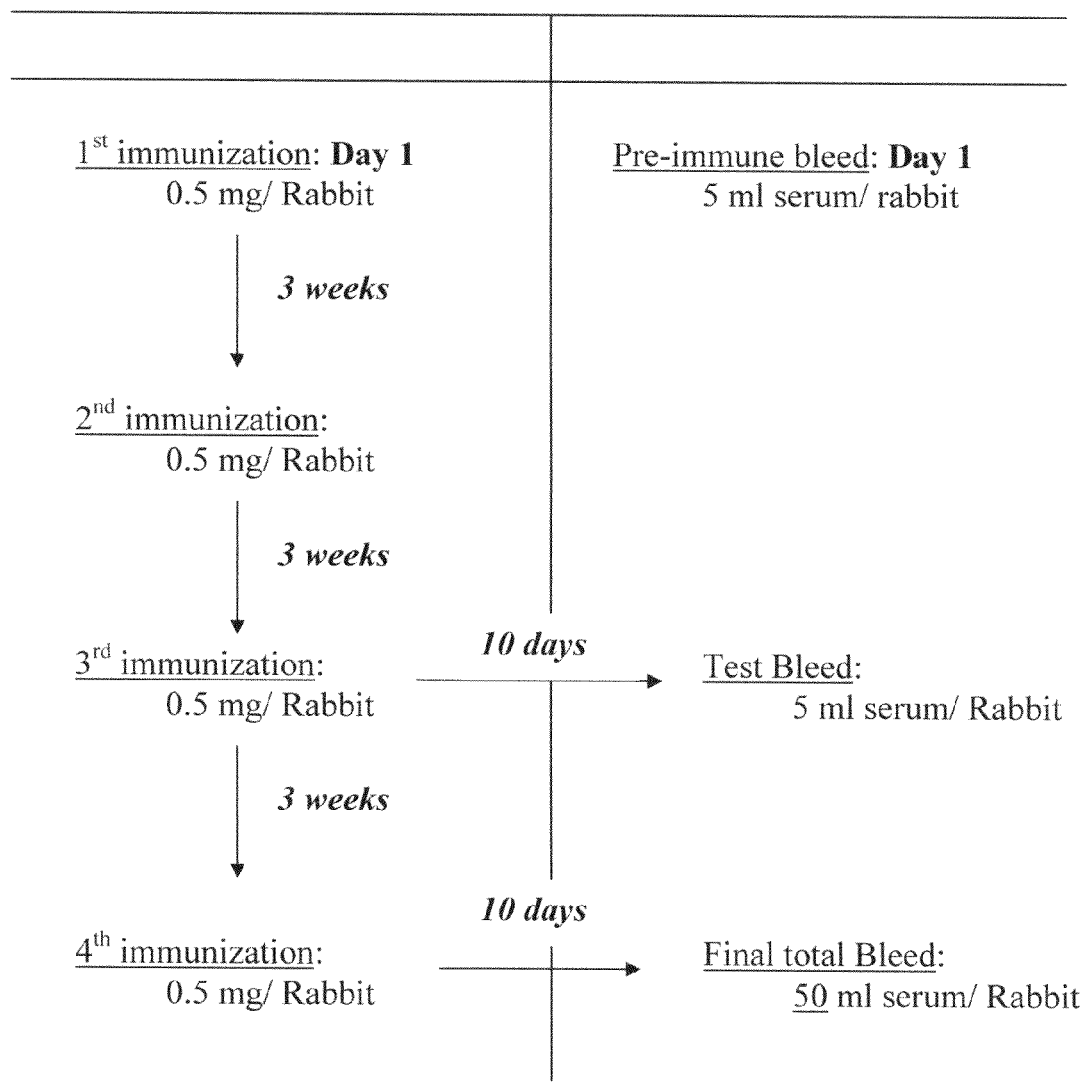
FIG. 13 is a diagram showing the procedure used to generate the anti-p-beta-cat-Ser552 polyclonal antibody according to the present invention.

The amount of p-β-catenin immunogen composition used in the production of polyclonal antibodies varies depending upon the nature of the immunogen (e.g. position of phosphorylation) as well as the animal used for immunization. A variety of routes can be used to administer the present p-β-catenin immunogen; subcutaneous, intramuscular, intradermal, intravenous, intraperitoneal and intrasplenic. The production of polyclonal antibodies may be monitored by sampling blood of the immunized animal at various points following immunization. A second, booster injection, may also be given. The process of boosting and tittering is repeated until a suitable titer is achieved. When a desired titer level is obtained, the immunized animal can be bled and the serum isolated and stored. The animal can also be used to generate monoclonal antibodies. A procedure used to generate the anti-p-beta-cat-Ser552 antibody is set forth in FIG. 13 and is representative of the kinds of procedures that may be used to generate the polyclonal antibodies of the present invention.

As is well known in the art, the immunogenicity of a particular composition can be enhanced by the use of non-specific stimulators of the immune response, known as adjuvants. Exemplary adjuvants include complete Freund's adjuvant, a non-specific stimulator of the immune response containing killed *Mycobacterium tuberculosis*; incomplete Freund's adjuvant; and aluminum hydroxide adjuvant.

It may also be desired to boost the host immune system as may be achieved by associating p-β-catenin with, or coupling p-β-catenin to, a carrier. Exemplary carriers include, e.g., keyhole limpet hemocyanin (KLH) and bovine serum albumin (BSA). Other albumins such as, e.g., ovalbumin, mouse serum albumin or rabbit serum albumin can also be used as carriers. As is also known in the art, a given composition may vary in its immunogenicity. However, the generation of antibodies against p-β-catenin is not particularly difficult.

B. Monoclonal Antibodies

Various methods for generating monoclonal antibodies (MAbs) are also well known in the art. The most standard monoclonal antibody generation techniques generally begin along the same lines as those for preparing polyclonal antibodies (Antibodies: A Laboratory Manual, Cold Spring Harbor Laboratory, 1988; incorporated herein by reference). A polyclonal antibody response is initiated by immunizing an animal with an immunogenic p-β-catenin composition and, when a desired titer level is obtained, the immunized animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with the selected p-β-catenin immunogen composition, wherein phosphorylation is at the desired position, most preferably $Ser^{552}$. The immunizing composition is administered in a manner effective to stimulate antibody-producing cells. Rodents such as mice and rats are preferred animals, however, the use of rabbit, sheep, and frog cells is also possible. The use of rats may provide certain advantages (Goding, 1986, pp. 60-61; incorporated by reference herein), but mice are preferred, for example BALB/c mice are often a strain of choice as this is routinely used and generally gives a higher percentage of stable fusions.

Following immunization, somatic cells with the potential for producing p-β-catenin antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically a spleen from an immunized mouse contains approximately $5 \times 10^7$ to $2 \times 10^8$ lymphocytes.

Any one of a number of myeloma cells may be used as are known to those of skill in the art (Goding, pp. 65-66 (1986); Campbell, pp. 75-83 (1984); each of which is incorporated herein by reference). For example, where the immunized animal is a mouse, one may use P3-X63/Ag8, X63-Ag8.653, NS1/1-Ag4-1, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

Methods for generating hybrids of antibody-producing spleen or lymph node cells and myeloma cells usually comprise mixing somatic cells with myeloma cells in a 4:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976; each of which is incorporated by reference herein), and those using polyethylene glycol (PEG), such as 37% (v/v) PEG, by Gefter et al (1977; incorporated by reference herein). The use of electrically induced fusion methods is also appropriate (Goding, pp. 71-74 (1986); incorporated by reference herein).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

An exemplary selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired anti-p-β-catenin reactivity. The assay should be sensitive, simple, and rapid, such as radioimmunoassay, enzyme immunoassays, cytotoxicity assays, plaque assays, dot immunobinding assays, and the like.

The selected hybridomas would then be serially diluted and cloned into individual anti-p-β-catenin antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means will generally be further purified, e.g., using filtration centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

Thus, one embodiment of the invention is a purified antibody that binds specifically to β-catenin phosphorylated at amino acid position Serine$^{552}$. In the present invention, "Serine$^{552}$", "Ser$^{552}$," and "S$^{552}$" are used interchangeably and are intended to mean the serine amino acid at position 552 of the murine β-catenin polypeptide (SEQ ID NO:6). Unless otherwise specifically limited by context, a reference to "S$^{552}$" or an antibody raised against an antigen containing a phosphorylated form of S$^{552}$ is intended to include ortholog epitopes, particularly the human ortholog epitope thereof. As discussed in more detail below, β-catenin is highly conserved among many species. Indeed, there is only a single amino acid difference between the human (SEQ ID NO:7) and murine (SEQ ID NO:6) β-catenin sequences. And, the β-cat-p-S$^{552}$ epitope (SEQ ID NO:5) used to generate the anti-p-beta-cat-Ser552 antibody of the present invention is 100% conserved between the murine and the human. SEQ ID NO:5, which corresponds to amino acid positions 544-555 of the murine β-catenin (SEQ ID NO:6) is identical to amino acid positions 544-555 of the human β-catenin (SEQ ID NO:7).

In the present invention, a "purified" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. A purified antibody includes the antibody in situ within recombinant cells because at least one component of the antibody's natural environment will not be present. Ordinarily, however, purified antibody will be prepared by at least one purification step.

An antibody that "specifically binds to", is "specific for", or "binds specifically to" a particular polypeptide or an epitope on a particular polypeptide is one that binds to that particular polypeptide or epitope on a particular polypeptide without substantially binding to any other polypeptide or polypeptide epitope. In the present invention, "anti-p-beta-cat-Ser552" is used interchangeably with "anti-p-beta-cat-Ser$^{552}$" "anti-p-Ser$^{552}$-catenin", "anti-p-b-cat-Ser552", "anti-pSer552-β-catenin" and the like (including similar combinations of "p", "β" or "beta", "cat" or "catenin", and "Ser 552", "Serine 552", "S$^{552}$" or "Ser$^{552}$").

As set forth previously, in the present invention, the purified antibody may be a monoclonal or a polyclonal. The antibody may be raised in or against any convenient species, such as a mammal, including a rodent or primate. Preferably, the antibody is a human, mouse, rabbit, or rat antibody.

In one aspect of this embodiment, the antibody specifically binds to an epitope that is within the sequence [C]HQDTQRRTSMGG (SEQ ID NO:5) or the sequence QDTQRRTSMGGTQQQ (SEQ ID NO:4). Such an antibody may be monoclonal or polyclonal. Preferably, such an antibody is a human, mouse, rabbit, or rat antibody.

Other antibody-like molecules are also within the scope of the present invention. For example, in another embodiment, the invention is a purified molecule that binds specifically to β-catenin phosphorylated at amino acid position Serine$^{552}$. In this aspect, the purified molecule may be any chemical entity, biological or synthetic, that is capable of specifically binding to β-catenin phosphorylated at amino acid position Serine$^{552}$. Such antibody-like molecules include, e.g., an affibody (see, e.g., Wikman et al., Selection and characterization of HER2/neu-binding affibody ligands, Protein Eng Des Sel, 17:455-462 (2004) and Affibody (Bromma, Sweden)), an affilin molecule (see, e.g., Hey et al., Artificial, non-antibody binding proteins for pharmaceutical and industrial applications. Trends Biotechnol, 23:514-522 (2005) and Scil Proteins (Halle, Germany)), antibody mimetics (such as adnectins, fibronectin based "addressable" therapeutic binding molecules from, e.g., Compound Therapeutics, Inc. (see, e.g., Xu et al., Directed evolution of high-affinity antibody mimics using mRNA display, Chem Biol, 9:933-942 (2002) and Compound Therapeutics (Waltham, Mass.)), an anticalin (see, e.g., Schlehuber and Skerra, Tuning ligand affinity, specificity, and folding stability of an engineered lipocalin variant—a so-called "anticalin"—using a molecular random approach, Biophys Chem, 96:213-228 (2002) and Pieris (Freising, Germany)), a designed ankyrin repeat protein (DARPin) (see, e.g., Binz et al., Designing repeat proteins: well-expressed, soluble and stable proteins from combinatorial libraries of consensus ankyrin repeat proteins, J. Mol Biol, 332:489-503 (2003) and Molecular Partners (Zurich, Switzerland)), an evibody (see, e.g., Irving et al., Ribosome display and affinity maturation: from antibodies to single V-domains and steps towards cancer therapeutics, J. Immunol. Methods, 248:31-45 (2001) and Evogenix (Sydney, Australia)), a knottin (see, e.g., Craik et al., The cystine knot motif in toxins and implications for drug design, Toxicon, 39:43-60 (2001)), a Kunitz-type domain (see, e.g., Dennis and Lazarus, Kunitz domain inhibitors of tissue factor-factor VIIa I. Potent inhibitors selected from libraries by phase display, J. Biol. Chem., 269:22129-22136 (1994) and Dyax (Cambridge, Mass.)), a maxibody (avimer) (see, e.g., Silverman et al., Multivalent avimer proteins evolved by exon shuffling of a family of human receptor domains, Nat Biotechnol, 23:1556-1561 (2005) and Avidia (Mountain View, Calif.)), domain antibodies (the smallest functional fragment of a naturally occurring single-domain antibody (such as, e.g., nanobodies; see, e.g., Cortez-Retamozo et al., Cancer Res. 2004 Apr. 15; 64(8):2853-7; Conrath et al., Antigen binding and solubility effects upon the veneering of a camel VHH in framework-2 to mimic a VH, J Mol Biol, 350:112-125 (2005); and Ablynx (Ghent, Belgium)), a tetranectin (having, e.g., a tetranectin monomeric or trimeric human C-type lectin domain scaffold from e.g., Borean Pharma (Aarhus, Denmark)), a trans-body (having a serum transferrin scaffold from, e.g., BioRexis (King of Prussia, Pa.)), and a V(NAR) (a variable domain of new antigen receptor (Holliger and Hudson, Engineered antibody fragments and the rise of single domains, Nat Biotechnol, 23:1126-1136 (2005)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253(5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307(1):198-205. Additional discussion of related principles, methods, etc., that may be applicable in the context of this invention are provided in, e.g., Fassina, Immunomethods. October 1994; 5(2):121-9.

In the present invention, anticalins can be screened for specific binding to β-catenin phosphorylated at amino acid position Serine$^{552}$. Anticalins are ligand-binding proteins that have been constructed based on a lipocalin scaffold (Weiss, G. A. and H. B. Lowman (2000) Chem. Biol. 7:R177-R184; Skerra, A. (2001) J. Biotechnol. 74:257-275). The protein architecture of lipocalins can include a beta-barrel having eight antiparallel beta-strands, which supports four loops at its open end. These loops form the natural ligand-binding site of the lipocalins, a site which can be re-engineered in vitro by amino acid substitutions to impart novel binding specificities. The amino acid substitutions can be made using methods known in the art, and can include conservative substitutions (e.g., substitutions that do not alter binding specificity) or substitutions that modestly, moderately, or significantly alter binding specificity.

In another aspect, the purified molecule may be a nucleic acid, such as for example, an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270, 163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

In a further embodiment, the present invention is a purified antibody that binds to a polypeptide consisting of SEQ ID NO:4 or SEQ ID NO:5, which are derived from the mouse. The present invention also includes purified antibodies that bind to other mammalian orthologs of these sequences, particularly the human ortholog of these sequences. Indeed, as described in more detail herein and in the examples below, the epitope encoding the Akt phosphorylation site at amino acid position $S^{552}$ on the murine β-catenin is well conserved across both mammalian and non-mammalian species. Both SEQ ID NO:4 and 5 are identical in, e.g., the mouse and human. In another preferred embodiment, the invention is the polyclonal anti-p-beta-cat-Ser552 antibody, which is described in more detail in the Examples. This antibody has been deposited under the terms of the Budapest Treaty as disclosed in more detail below.

V. Methods

In another embodiment of the invention, there is provided a method of making an antibody. This method comprises immunizing a non-human animal, such as a rabbit, with an immunogenic fragment from an Armadillo domain of β-catenin that is phosphorylated by Akt. In the present invention, the immunogenic fragment may be any fragment of the β-catenin polypeptide that includes $S^{552}$ or an ortholog thereof and is able to raise an immune response, either alone or in combination with an adjuvant and/or carrier, when placed in a foreign host. Preferably, the immunogenic fragment consists of SEQ ID NO:4 or 5 or an immunogenic fragment that contains SEQ ID NO:4 or 5 plus or minus up to 5 additional amino acids.

In another embodiment, the invention is a method of detecting a phosphorylation state of β-catenin. This method comprises determining whether Serine$^{552}$ of β-catenin is phosphorylated. As used herein, "a phosphorylation state of β-catenin" refers particularly to Akt-mediated phosphorylation of β-catenin. More particularly, "a phosphorylation state of β-catenin" refers to Akt-mediated phosphorylation of β-catenin at amino acid position $S^{552}$ of SEQ ID NO:6 (gi: 31419848), which is the β-catenin amino acid sequence from Mus musculus or a mammalian ortholog thereof, particularly a human ortholog thereof, such as SEQ ID NO:7 (gi: 4503131).

In this embodiment, the determining step comprises contacting β-catenin with an antibody or other molecule that binds specifically to β-catenin phosphorylated at amino acid position Serine$^{552}$ or to the analogous sequence of a mammalian ortholog thereof, particularly a human ortholog. In this aspect, "contacting" means bringing the antibody into intimate contact with the β-catenin such that if the Serine$^{552}$ (or analogous amino acid in a mammalian ortholog, such as a human ortholog) has been phosphorylated, the antibody will specifically bind to the epitope containing the phosphorylated Serine$^{552}$. The contacting step may be accomplished using any known method for presenting an antibody to its antigen. For example, in the case of an in vitro diagnostic assay, the antibody may be pipetted or otherwise distributed into an apparatus such as for example a slide, well, tube, etc. containing a sample, e.g., a tissue or fluid sample from a patient, such as a human patient or from a cell line or a primary culture.

It is also preferred that the antibody is the polyclonal anti-p-beta-cat-Ser552 antibody, which has been deposited with the ATCC under accession number PTA-9077.

In another aspect, the method includes the use of another molecule, i.e., an antibody-like molecule that binds specifically to β-catenin phosphorylated at amino acid position Serine$^{552}$ or to the analogous sequence of a mammalian ortholog thereof, particularly a human ortholog. Such a molecule is selected from the group consisting of an affibody, an affilin molecule, an adnectin, an anticalin, a designed ankyrin repeat protein (DARPin), a domain antibody, an evibody, a knottin, a Kunitz-type domain, a maxibody, a nanobody, a tetranectin, a trans-body, or a V(NAR). The molecule may also be selected from the group consisting of an aptamer (RNA or DNA), an intramer, and a spiegelmer.

In a further aspect of this method, the antibody or molecule is used in an assay selected from the group consisting of an immunohistochemical assay, an immunofluorescence assay, an enzyme-linked immunosorbent assay (ELISA), an immunoprecipitation assay, or a Western blot. Preferably, the assay is a diagnostic assay for a mammal, particularly a human. In this regard, the method further comprises correlating the presence of phosphorylation at Serine$^{552}$ or at the analogous amino acid in a mammalian ortholog, such as a human ortholog, to activation of a β-catenin pathway. In the present invention, if the phosphorylation at $S^{552}$ is at least about two-fold higher, such as, e.g., from about 3-fold to about 10-fold (or more) higher compared to control, such elevated phosphorylation at $S^{552}$ may be correlated or associated with the presence of a disease as defined herein. The correlation step may be accomplished using standard techniques in the art and may be carried out by a technician, or a physician, or using a system designed to detect changes in the phosphorylation state of β-catenin using an antibody of the present invention.

This aspect of the invention further includes correlating the presence of phosphorylation at Serine$^{552}$ or at the analogous amino acid in a mammalian ortholog, such as a human ortholog, to a disease associated with a decrease in or loss of function of PTEN or mutations in PTEN. A non-limiting example of a disease associated with a decrease in or loss of function of PTEN or mutations in PTEN is intestinal polyposis.

VI. Kits

It is envisioned that the antibodies of the invention will be useful for detecting cancer stem cells, mutant ISCs, examining the PTEN/Akt pathway, identifying target sites for new anti-tumor therapeutics, for screening such therapeutics for effectiveness, and for other diagnostic assays for, e.g., intestinal polyposis. A variety of kits can be formed using the anti-p-beta-cat-Ser552 antibody described herein either alone or in combination with one or more additional antibodies. For example, the anti-p-beta-cat-Ser552 antibody may be provided separately or together with another antibody that also detects phosphorylated β-catenin. Preferably this latter antibody will detect phosphorylation at T217, T332, S673, or at another site within the Armadillo R10 repeat of β-catenin or at analogous site(s) in other mammalian orthologs, such as, e.g., a human ortholog. Where a second phosphorylation site is within R10 then the second phosphorylation site will be within 22 amino acids of S552, more preferably within 21, 20, 19, 18, 17, 16, 15, 14, 13, 12, 11, 10, 9, 8, 7, 6, or even 5 amino acids of S552. It is less preferred, but within the scope of the invention, for the second phosphorylation site to be within 5, 4, 3, or 2 amino acids of S552. Alternatively, the antibody may detect phosphorylated S552 and a second site of phosphorylation, wherein the second site is one of the aforementioned.

Kits are described for detection of β-catenin in which either up-regulated or down-regulated nuclear β-catenin, as described in the Examples herein, is indicative of mutant or variant ISCs. Such mutant ISCs are indicative of stem cells that are likely to give rise to polyps or recurring neoplasia. Kits will detect the presence or absence of mutant ISCs. The kit will preferably have a container and at least one antibody, preferably the anti-p-beta-cat-Ser552 antibody described herein.

The kit will also detect a mutant ISC containing an inactive PTEN protein or gene. Kits for detection and quantitation of the presence in intestinal cells of markers such as PTEN, P-PTEN, AKT, P-AKT, Tert, β-catenin, and 14-3-3ζ polypeptide and nucleic acid markers will be formed. These kits can be used for detection and quantitation of markers associated with intestinal cell activation, proliferation, differentiation, apoptosis, polyposis, and tumor formation. Specifically, immunodiagnostics and nucleic acid probe kits for mutant PTEN intestinal cell expression of the foregoing polypeptide markers will be made and used. In addition, the present invention includes diagnostic methods and kits for the prediction and assessment of intestinal polyposis and tumorigenesis. These foregoing kits may be used either in vitro or in vivo.

In another embodiment, there is provided a kit for detecting phosphorylation at Serine$^{552}$ of β-catenin. This kit comprises a purified antibody that binds specifically to β-catenin phosphorylated at amino acid position Serine$^{552}$ (e.g., the anti-p-beta-cat-Ser552 antibody) and instructions on how to use the antibody. In one aspect, the antibody is labeled as described above. In another aspect, the kit may further include one or more additional antibodies that bind specifically to other (i.e., non p-S$^{552}$ phosphorylation sites on β-catenin) and/or control antibodies. The kit may further include various other reagents (e.g., buffers) or apparatus for carrying out, e.g., human diagnostic methods with the anti-p-beta-cat-Ser552 antibody.

Typically, the antibody and kit will be packaged in a manner suitable for storage and distribution.

In summary, hybridization methodology and kits for the detection, identification, and quantification of PTEN mutant cells using anti-p-beta-cat-Ser552 antibody, inter alia, are set forth herein. Using these methods, PTEN Wt and mutant cells can be identified, characterized, and quantified.

DEFINITIONS

Unless defined otherwise, all technical and scientific terms used herein have the meaning commonly understood by a person skilled in the art to which this invention belongs at the time of filing. The following references provide one of skill with a general definition of many of the terms used in this invention: Singleton et al., *Dictionary of Microbiology and Molecular Biology* (2nd Ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless otherwise specified.

Activated mutant is a post-recombination organism, tissue, or cell wherein the mutant is obtained by injection of a recombination activator into a conditional mutant organism, tissue, or cell to induce a mutation event that results in inactivation of the targeted gene. For example, an activated PTEN mutant organism is a post-excision organism which resulted from injection of PolyI:C into a conditional PTEN mutant organism to yield a nonfunctional PTEN gene.

An activator is a molecule that can induce proliferation, self-renewal, cell division, or differentiation in a cell. The activator may optionally induce polyposis or apoptosis in a cell. An intestinal stem cell activator generally induces proliferation or cell division.

Allele is a shorthand form for allelomorph, which is one of a series of possible alternative forms for a given gene differing in the DNA sequence and affecting the functioning of a single product.

An amino acid (aminocarboxylic acid) is a component of proteins and peptides. All amino acids contain a central carbon atom to which an amino group, a carboxyl group, and a hydrogen atom are attached. Joining together of amino acids forms polypeptides. Polypeptides are molecules containing up to 1000 amino acids. Proteins are polypeptide polymers containing 50 or more amino acids.

An antigen (Ag) is any molecule that can bind specifically to an antibody (Ab). Ags can stimulate the formation of Abs. Each Ab molecule has a unique Ag binding pocket that enables it to bind specifically to its corresponding antigen. Abs may be used in conjunction with labels (e.g., enzyme, fluorescence, radioactive) in histological analysis of the presence and distribution of marker Ags. Abs may also be used to purify or separate cell populations bearing marker Ags through methods, including fluorescence activated cell sorter (FACS) technologies. Abs that bind to cell surface receptor Ags can inhibit receptor-specific binding to other molecules to influence cellular function. Abs are often produced in vivo by B cells and plasma cells in response to infection or immunization, bind to and neutralize pathogens, or prepare them for uptake and destruction by phagocytes. Abs may also be produced in vitro by cultivation of plasma cells, B cells or by utilization of genetic engineering technologies.

BMPs constitute a subfamily of the transforming growth factor type beta (TGF-β) supergene family and play a critical role in modulating mesenchymal differentiation and inducing the processes of cartilage and bone formation. BMPs induce ectopic bone formation and support development of the viscera. Exemplary BMPs include those listed by the NCBI, such as human BMP-3 (osteogenic) precursor (NP001192), mouse BMP-6 (NP031582), mouse BMP-4 (149541), mouse BMP-2 precursor (1345611), human BMP-5 preprotein (NP 066551.1), mouse BMP-6 precursor (1705488), human BMP-6 (NP 001709), mouse BMP-2A (A34201), mouse BMP-4 (461633), and human BMP-7 precursor (4502427).

Bmpr1a receptor, or Bmpr1a, is defined as the bone morphogenetic protein receptor, type 1A. Bmpr1a is a regulator of chondrocyte differentiation, down stream mediator of Indian Hedgehog, TGF-β superfamily, and activin receptor-like kinase 3. Binding a ligand to the receptor induces the formation of a complex in which the Type II BMP receptor (Bmpr1b receptor) phosphorylates and activates the Type I BMP receptor (Bmpr1a receptor). Bmpr1a receptor then propagates the signal by phosphorylating a family of signal transducers, the Smad proteins. The Bmpr1a gene encodes the Bmpr1a receptor. Bmpr1a binds to BMP and Noggin.

PTEN mutant organism is defined as an organism lacking a functional PTEN gene or a conditionally activated PTEN gene that can be rendered nonfunctional, where a nonfunctional PTEN gene is one that encodes an inactive PTEN protein. An example of such an organism is the Mx1-Cre$^+$ PTEN$^{fx/fx}$ mutant mouse.

A conditional mutant is a pre-recombination organism, tissue, or cell wherein injection of a recombination activator into the conditional mutant organism, tissue, or cell induces a mutation event that results in inactivation of the targeted gene, resulting in formation of an activated Bmpr1a mutant organism.

A conditional PTEN mutant knock-out organism can be a pre-recombination or post-recombination PTEN mutant organism. An example of a conditional PTEN mutant knock-out organism is a Mx1-Cre$^+$Bmpr1a$^{fx/fx}$ or Mx1-Cre$^+$ Bmpr1a$^{fx/fx}$ Z/EG organism. The mutant organism may be a mouse. Upon administration of a recombination activator, such as PolyI:C, to the pre-recombination PTEN mutant organism, a post-recombination PTEN mutant organism is formed in which the cells may contain a mutant PTEN nucleic acid sequence. The recombination activator may be administered either prenatally or postnatally to induce PTEN mutation in the cells.

Differentiation occurs when a cell transforms itself into another form. For example, an ISC may differentiate into cells of the mucosal or columnar differentiation pathways. An ISC may differentiate into a mucosal progenitor cell, which gives rise to a mucus-secreting goblet cell.

Expression cassette (or DNA cassette) is a DNA sequence that can be inserted into a cell's DNA sequence. The cell in which the expression cassette is inserted can be a prokaryotic or eukaryotic cell. The prokaryotic cell may be a bacterial cell. The expression cassette may include one or more markers, such as Neo and/or LacZ. The cassette may contain stop codons. In particular, a Neo-LacZ cassette is an expression cassette that can be placed in a bacterial artificial chromosome (BAC) for insertion into a cell's DNA sequence. Such expression cassettes can be used in homologous recombination to insert specific DNA sequences into targeted areas in known genes.

A gene is a hereditary unit that has one or more specific effects upon the phenotype of the organism; and the gene can mutate to various allelic forms. The gene is generally comprised of DNA or RNA.

Homolog relates to nucleotide or amino acid sequences which have similar sequences and that function in the same way.

A host cell is a cell that receives a foreign biological molecule, including a genetic construct or antibody, such as a vector containing a gene.

A host organism is an organism that receives a foreign biological molecule, including a genetic construct or antibody, such as a vector containing a gene.

Intestinal epithelial stem cell (ISC) is an intestinal stem cell that is distinguishable from progeny daughter stem cells. ISCs can be induced by an activator to undergo proliferation or differentiation. The ISC activator may be produced endogenously by another intestinal cell, such as a mesenchymal cell. Alternatively, the ISC activator may also be exogenously administered to the cell. ISCs may be located at the base of the villi, in or adjacent to the crypt region of the small and large intestine.

Intestinal tissue is isolated large or small intestine tissue obtained from an organism, and this tissue possesses villi, lumen, crypts, other intestinal microstructures, or portions thereof. Intestinal tissue can be derived from either Wt or mutant organisms. Intestinal tissue includes intestinal stem cells. Intestinal tissue may be cultivated in vitro or in vivo.

Knock-out is an informal term coined for the generation of a mutant organism (generally a mouse) containing a null or inactive allele of a gene under study. Usually the animal is genetically engineered with specified wild-type alleles replaced with mutated ones. Knock-out also refers to the mutant organism or animal. The knock-out process may involve administration of a recombination activator that excises a gene, or portion thereof, to inactivate or "knock out" the gene. The knock-out organism containing the excised gene produces a nonfunctional polypeptide.

A label is a molecule that is used to detect or quantitate a marker associated with a cell or cell type. Labels may be nonisotopic or isotopic. Representative, nonlimiting nonisotopic labels may be fluorescent, enzymatic, luminescent, chemiluminescent, or calorimetric. Exemplary isotopic labels may be $H^3$, $C^{14}$, or $P^{32}$. Enzyme labels may be horseradish peroxidase, alkaline phosphatase, or β-galactosidase labels conjugated to anti-marker antibodies. Such enzymeantibody labels may be used to visualize markers associated with cells in intestinal or other tissue. An exemplary fluorescent label is green fluorescent protein (GFP).

A marker is an indicator that characterizes either a cell type or a cell that exists in a particular state or stage. A stem cell marker is a marker that characterizes a specific cell type that can possess a cell function such as self-renewal, proliferation, differentiation, or apoptosis. The marker may be external or internal to the cell. An external marker may be a cell surface marker. An internal marker may exist in the nucleus or cytoplasm of the cell. Markers can include, but are not limited to polypeptides or nucleic acids derived from PTEN, P-PTEN, AKT, PAKT, Tert, β-catenin, GFP, and LacZ molecules, and mutant molecules thereof. Markers may also be antibodies to the foregoing molecules, and mutants thereof. For example, antibodies to PTEN and p-catenin can serve as markers that indicate the presence of these respective molecules within cells, on the surface of cells, or otherwise associated with cells. GFP and LacZ marker sites can indicate that recombination occurs in a target gene, such as the PTEN gene.

A mutation is defined as a genotypic or phenotypic variant resulting from a changed or new gene in comparison with the Wt gene. The genotypic mutation may be a frame shift, substitution, loss of function, or deletion mutation, which distinguishes the mutant gene sequence from the Wt gene sequence.

A mutant is an organism bearing a mutant gene that expresses itself in the phenotype of the organism. Mutants may possess either a gene mutation that is a change in a nucleic acid sequence in comparison to Wt, or a gene mutation that results from the elimination or excision of a sequence. In addition polypeptides can be expressed from the mutants.

PolyI:C is an interferon inducer consisting of a synthetic, mismatched double-stranded RNA. The polymer is made of one strand each of polyinosinic acid and polycytidylic acid. PolyI:C is 5'-Inosinic acid homopolymer complexed with 5'-cytidylic acid homopolymer (1:1). PolyI:C's pharmacological action includes antiviral activity.

A polypeptide is an amino acid polymer comprising at least two amino acids.

A post-excision mutant organism is an organism, a targeted gene, or sections thereof, wherein the targeted gene or section has been excised by recombination. The post-excision organism is called a "knock-out" organism. Administration of a recombination activator, such as PolyI:C or interferon, can induce the recombination event resulting in target gene excision.

Proliferation occurs when a cell divides and results in progeny cells. Proliferation can occur in the self-renewal or proliferation zones of the intestinal villus. Stem cells may undergo proliferation upon receipt of molecular signals such as those transmitted through Bmpr1a cellular receptor.

PTEN family nucleotide sequence includes, but is not limited to, the following: PTEN, PI3K, AKT, Tert, β-catenin, P27, and BAD nucleic acid sequences, and mutant sequences derived therefrom. PTEN pathway polypeptides or proteins are those that are encoded by PTEN pathway genes, which include, but are not limited to the following: PTEN, PI3K, AKT, Tert, β-catenin, P27, and BAD genes, and mutant genes derived therefrom. The PTEN pathway is also called the PTEN/PI3K/AKT/Tert/β-catenin pathway. The PTEN pathway is regulated by Noggin and BMP, which function in a diametrically opposite manner. Noggin binding to Bmpr1a receptor releases BMP inhibition of ISC function, through a cascade of increased levels of activated P-PTEN, P-AKT, β-catenin, and Tert, resulting in ISC proliferation necessary to regenerate dead or lost intestinal epithelial cells in the intestine. In contrast, high BMP activity at the tips of the villi induces increased BAD activity and intestinal cell death;

whereas Bmpr1a mutant villi, nonresponsive to BMP signaling, exhibited decreased apoptosis due to loss of BAD signaling.

A selectable marker is a marker that is inserted in a nucleic acid sequence that permits the selection and/or identification of a target nucleic acid sequence or gene. A selectable marker associated with the Bmpr1a gene mutation may identify the presence of the Bmpr1a mutation.

A stem cell is defined as a pluripotent or multipotent cell that has the ability to divide (self-replicate) or differentiate for indefinite periods—often throughout the life of the organism. Under the right conditions, or given optimal regulatory signals, stem cells can differentiate to transform themselves into the many different cell types that make up the organism. Stem cells may be distinguishable from progeny daughter cells by such traits as BrdU retention and physical location/orientation in the villus microenvironment. Multipotential or pluripotential stem cells possess the ability to differentiate into mature cells that have characteristic attributes and specialized functions, such as hair follicle cells, blood cells, heart cells, eye cells, skin cells, or nerve cells. A stem cell population is a population that possesses at least one stem cell.

Support is defined as establishing viability, growth, proliferation, self-renewal, maturation, differentiation, and combinations thereof, in a cell. In particular, to support an ISC population refers to promoting viability, growth, proliferation, self-renewal, maturation, differentiation, and combinations thereof, in the ISC population. Support of a cell may occur in vivo or in vitro. Support may exclude apoptosis or cell death-related events.

A vector is an autonomously self-replicating nucleic acid molecule that transfers a target nucleic acid sequence into a host cell. The vector's target nucleic acid sequence can be a Wt or mutant gene, or fragment derived therefrom. The vector can include a gene expression cassette, plasmid, episome, or fragment thereof. Gene expression cassettes are nucleic acid sequences with one or more targeted genes that can be injected or otherwise inserted into host cells for expression of the encoded polypeptides. Episomes and plasmids are circular, extrachromosomal nucleic acid molecules, distinct from the host cell genome, which are capable of autonomous replication. The vector may contain a promoter, marker or regulatory sequence that supports transcription and translation of the selected target gene. Viruses are vectors that utilize the host cell machinery for polypeptide expression and viral replication.

Wild type is the most frequently observed phenotype in a population, or the one arbitrarily designated as "normal." Often symbolized by "+" or "Wt." The Wt phenotype is distinguishable from mutant phenotype variations.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods

Animal Model.

All the animal work was performed in compliance with protocols approved by the IACUC at Stowers Institute for Medical Research. Induction of PTEN conditional inactivation was performed following the procedure described previously in He, et al., "BMP signaling inhibits intestinal stem cell self-renewal through suppression of WNT-beta-catenin signaling", Nat. Genet. 36: 1117-1121 (2004); He et al., "PTEN-deficient intestinal stem cells initiate intestinal polyposis", Nat. Genet. 39: 189-198 (2007); and in U.S. patent application Ser. No. 10/860,501, filed Jun. 3, 2004, each of which is incorporated herein by reference. Briefly, Mx1-Cre:Pten$^{fl/fl}$ mice and control animals were injected intraperitoneally with poly inosinecytidine at a dosage of 250 µg/mouse for 5 times at an interval of every other day, beginning at or prior to weaning. Verification of targeting efficiency was performed using the following primers: P1: actcaaggcagggatgagc (SEQ ID NO: 1); P2: aatctagggcctcttgtgcc (SEQ ID NO: 2); P3: gcttgatatcgaaftcctgcagc (SEQ ID NO: 3). Amplification products were Wt: 900 bp, Loxp: 1000 bp, and No PTEN Loxp:300 bp.

Intestinal Specimen Preparation and Immunohistochemical/Immunofluorescent Staining.

This work was performed following the procedures described in He, et al., "BMP signaling inhibits intestinal stem cell self-renewal through suppression of WNT-beta-catenin signaling", Nat. Genet. 36: 1117-1121 (2004) and in U.S. patent application Ser. No. 10/860,501, filed Jun. 3, 2004, both of which are incorporated herein, with the following alterations.

Immunohistochemical Staining.

The condition for unmasking the epitopes varied depending on the primary antibody used. The immunohistochemical staining of nuclear β-catenin for □β-cat-pS552 was as follows. Paraffin-embedded intestinal tissues were deparaffinized, rehydrated, and blocked using a 3-serum blocker (2% mouse serum+10% goat serum+10% donkey serum in PBS) for 30 minutes to 1 hour. Antigen retrieval was performed in a Microwave oven (BioGnex, EZ Retriever™) for 10 Min. at 95° C. in Citrate buffer (pH 6.0; 82 ml of 0.1M sodium citrate/18 ml of 0.1M citric acid in 1000 ml distilled water). Samples were washed with distilled water 3 times; tissue was identified with a PAP pen (Biocare Medical Cat. No. PEN1111); and blocked with 3-serum blocker. Anti-p-beta-cat-Ser552 antibody (1:1000 dilution) was added (150 ul) onto the tissue sections until covered. Tissue was left at room temperature for 1 hour or at 4° C. for overnight. Tissue was then washed with PBS containing Tween20 for 15 minutes×3 times (total 45 minutes). Rabbit-HRP (DAKO, En Vision, Rabbit Peroxidase, K4003) was added, and the tissue was left at room temperature for 1 hour then washed with PBS containing Tween 20 for 15 minutes×3 times (total 45 minutes). Stained tissue was developed with DAB until the color developed on the tissue (3-5 minutes). Tissue was mounted with Crystal Mount (Biomeda Cat. No. M02) and air-dried, or mounted and covered with a cover slip using Cytoseal-60 (Richard Allen Cat. No. 8310-4), followed by air-drying.

The staining procedure for Np-NT β-catenin (Upstate Technology) was similar with the following differences. Antigen retrieval was performed in a Decloaking Chamber (Biocare Cat. No. DC2002) by decloaking in Citrate buffer (pH 6.0; 82 ml of 0.1M sodium citrate/18 ml of 0.1M citric acid in 1000 ml distilled water) using the following program: SP1 125° C. for 4 minutes and SP2 125° C. for another 1 minute.

After the program runs, the pressure will start to drop. After the pressure reached zero (0), 60 minutes were allowed to pass before opening the Decloaking Chamber. Slides were cooled to room temperature. The primary antibody (β-catenin, Upstate Cat. No. 05-665, mouse monoclonal antibody) was biotinylated as follows, using the Biotinylation Kit from DAKO (Cat. No. K3954). Antibody was left at room temperature for 30 minutes; 6 µl of blocking serum was added at room temperature for 10 minutes; and excess blocking serum was removed using a tissue. Antibody concentration was 1000 µg/ml: β-catenin 3 µl; Biotin 30 µl; Diluents (DAKO Cat. No. S0809) 118 µl. For the primary antibody 150 µl of the Biotinylated β-catenin Ab was added onto the tissue sections until covered. Tissue was then left at room temperature for 1 to 3 hours, then at 4° C. for 2 nights. For secondary antibody binding, the SV-HRP (DAKO Biotinylation Kit) was added, and tissues were left at room temperature for 1-2 hours, then at 4° C. overnight.

Immunofluorescent Staining.

Co-staining of 14-3-3ζ with Musashi and co-staining of Musashi with BrdU and β-catenin, p27kip1, was carried out following the method described in He, et al., "BMP signaling inhibits intestinal stem cell self-renewal through suppression of WNT-beta-catenin signaling", Nat. Genet. 36: 1117-1121 (2004) and in U.S. patent application Ser. No. 10/860,501, filed Jun. 3, 2004, both of which are incorporated herein by reference.

Tissue sections were incubated with primary antibodies overnight at 4° C. After several washes with 1×PBS, the slides were incubated in Cy™-2 conjugated AffiniPure donkey anti-rabbit IgG (1:300) and Cy™-3 conjugated AffiniPure donkey anti-sheep IgG (1:600) for 30 minutes at 37° C. (Jackson ImmunoResearch Laboratories, West Grove, Pa.). Slides were washed with 1×PBS, mounted, and viewed.

Top-Gal Staining.

Intestinal tissue were opened and washed thoroughly with PBS. The tissue will be fixed* in LacZ fixative buffer (0.4 ml 25% glutaraldehyde in 44.1 ml PBS with 0.5 ml 0.5M EGTA and 5 ml 1M $MgCl_2$) at 4° C. for 2 hours. (*All fixation were done at 4° C. on shaker/rotator). Rinse with PBS for three times and rinse with LacZ wash buffer (in 500 ml buffer, add 1 ml 1M $MgCl_2$, 5 ml 1% NaDOC, 5 ml 2% NP40, and 489 ml PBS). Stain in LacZ staining solution at 33° C. for 6 hours in dark. Staining solution (96 ml LacZ wash buffer, 4.0 ml 25 mg/ml X-gal [dissolved in DMSO], 0.21 g Potassium Ferro cyanide, 0.16 g Potassium Ferro cyanide). Wash with PBS for three times, and fix in Zinc Formalin. The rest of the procedure was the same as for paraffin section preparation as described above.

Whole Mount Immunofluorescent Staining.

Crypts were isolated following the procedure described by Grossman, et al., "New isolation technique to study apoptosis in human intestinal epithelial cells. Am. J. Pathol. 153: 53-62 and incorporated herein by reference. Isolated intestinal crypts were fixed in 4% paraformaldehyde for 1 hr at 4° C., and permeabilized using 0.5% Triton-X100 in PBS; and staining was following the procedures described above. The crypts were blocked by incubation in blocking buffer (Universal blocking reagent, BioGenex) for 1 hr. Primary antibodies were diluted in 0.5% Triton-X100 PBS and the crypts were incubated overnight at 4° C. with gentle agitation. Whole mount crypts were then washed for at least 2 hours in PBS containing Tween 20, changing the buffer several times. Fluorescent conjugated secondary antibodies were incubated in the same way. For counter-stain, the crypts were incubated with DAPI in PBS for 10 min, following by mounting with the aqueous mounting medium (biomedia). Images were acquired using a Zeiss 510 Confocal microscope, and reconstructed by 30 optical sections of each crypt.

Bioinformatics and Mass-Spectrometry.

To identify potential Akt phosphorylation sites in. β-catenin we used Scansite 2.0 and performed a medium stringency motif search of the human β-catenin protein sequence, which identified a single potential Akt (basophilic serine/threonine kinase) phosphorylation site (at $Ser^{552}$). The identified motif (QDTQRRTSMGGTQQQ (SEQ ID NO: 4); wherein the underlined S is $Ser^{552}$) is underlined and is identical in the human, mouse and rat β-catenin proteins. The procedure for analysis of phosphor-peptide using mass-spectrometry has been described previously. (Tao, W. A. et al., Quantitative phosphoproteome analysis using a dendrimer conjugation chemistry and tandem mass spectrometry. Nat Methods 2: 591-598 (2005).)

Raising and Purifying the Anti-p-Beta-Cat-Ser552 Antibody.

Mass-spectrometry analysis detected the phosphorylated $Ser^{552}$ in β-catenin after the purified β-catenin protein was incubated with Akt (Cell Signaling). A phosphor-peptide ($pSer^{552}$-Catnb: [C]HQDTQRRTpSMGG] (SEQ ID NO: 5)) was synthesized by Zymed; anti-serum was raised against the phosphor-peptide conjugated with Cys-KLH. As shown, the phosphor-peptide contains an optional cysteine ([C]), not present in the native sequence, which may be used for ease of processing, e.g., combining with KLH or for attaching to a column. The anti-serum was first purified using affinity column and passed the column filled with phosphor-peptide-matrix gel to enrich the anti-phospho-peptide antibody. Finally, the non-specific antibody was removed using the column filled with non-phosphor-peptide-matrix gel (Zymed).

Western Blot Analysis and Top-Gal Staining

Intestinal tissue was homogenized in 1 ml lysis cocktail (100 mM Tris-HCl, pH 6.8, 2% SDS and a proteinase inhibitor cocktail supplied by Roche). The supernatant was collected after centrifugation. Protein extracts (20 µg/well) were fractionated on SDS-PAGE gel and transferred onto nitrocellulose membrane. The membrane was blocked using casein blocker (Pierce) and was incubated with appropriate primary (p-Akt, 1:1000, p-GSK, 1:2000, Cyclin D1, 1:3000 [Cell Signaling], Active-β-catenin, 1:3000 [Upstate]; p27kip1, 1:4000 [Invitrogen]; p-β-catenin $S^{552}$, 1:2000 [Custom-made by Zymed]) and secondary antibodies (1:4,000 dilutions) in casein or 5% BSA blocker. The membrane was developed using chemiluminescent reagents (Pierce) after washing with TBS-T solution (TBS plus 0.05% Tween-20).

Microarray and RT-PCR Assays.

The procedure for both microarray and RT-PCR assays have been previously described by Akashi, et al., (2003) Transcriptional accessibility for genes of multiple tissues and hematopoietic lineages is hierarchically controlled during early hematopoiesis. Blood. 101, 383-389. Microarray analysis compared the gene expression profiles of polyp regions from three PTEN mutant animals with two control intestines. Genes were considered up-regulated or down-regulated if all of the following conditions were met: (1) There was at least a two-fold change in the average probe signal measured between controls and mutants; (2) There was no overlap between the ranges of mutant and control data; and (3) The control mean was outside the 95% confidence interval of the PTEN-mutant mean. By these criteria, 1243 known genes were up-regulated and 1,053 were down-regulated. Gene ontology terms were analyzed with Ontoexpress as described above. WebGestalt (see above) was also used to identify significantly enriched classes of ontology terms by BioCarta map. The additional up-regulated genes shown shared the enriched BioCarta term "Cell cycle: G1/S check point" (hypergeometric test. p=0.0496). The microarray signals were plotted with Heatmap Builder. Microarray analysis compared the gene expression profiles of polyp regions from three PTEN mutant animals with two control intestines. RT-PCR primers used were as follows:

```
c-Myc forward primer:
5'-GGACTGTATGTGGAGCGGTTTC-3'      (SEQ ID NO: 8)

c-Myc reverse primer:
5'-CTGGTAGGAGGCCAGCTTCTC-3'       (SEQ ID NO: 9)

Cyclin D1 forward primer:
5'-AGTTCATTTCCAACCCACCCTCA-3'     (SEQ ID NO: 10)

Cyclin D1 reverse primer:
5'-TCTGGAAAGAAAGTGCGTTGTGCG-3'    (SEQ ID NO: 11)

GAPDH forward primer:
5'-GAAGGTGAAGGTCGGAGTC-3'         (SEQ ID NO: 12)

GAPDH reverse primer:
5'-GAAGATGGTGATGGGATTTC-3'        (SEQ ID NO: 13)
```

Example 1

Induced Inactivation of PTEN Leads to Development of Intestinal Polyposis

To determine the time-course of PTEN loss in the conditional deletion system, Mx1-Cre: Pten$^{fl/fl}$ mice carrying a Z/EG reporter were generated, so that lineages from which Cre activity-deleted PTEN would be marked by the expression of green fluorescent protein (GFP). Gene deletion was induced at or before weaning with pIpC (see Methods above). GFP$^+$ cells were first detected three days after completion of pIpC treatment (day 3). Co-staining with the stem cell marker Musashi1 (Musashi) confirmed that recombination had occurred in ICS (FIG. 1B). Initially, GFP$^+$ epithelial cells were primarily clustered in the crypt bottom or located at the transition zone between crypts and villi (FIG. 1B, 1C). The GFP$^+$ domains expanded to include groups of crypts on day 5 (FIG. 1D), and finally were seen to encompass some entire crypts and villi on day 10 (FIG. 1E). A limited number of stromal cells were also shown to be GFP$^+$ (FIG. 1C). Successful targeting of the PTEN gene in the intestine was also confirmed by PCR analysis (FIG. 1H), which showed deletion of PTEN exon 5 encoding the phosphatase motif.

Multiple polyps (FIG. 1F) were detected regionally in the small intestinal tract of PTEN homozygous mutant mice (PTEN mutants; Mx1-Cre$^+$; Pten$^{fl/fl}$) one month after completion of pIpC injection (n=15), but were not observed in the control group (Mx1-Cre$^+$; Pten$^{fl/+}$ or Mx1-Cre$^-$; Pten$^{fl/fl}$). Histologically, the polyps exhibited a large excess of crypt-like units at their base as well as an aberrant positioning of crypts along the edges of villi. There were also insertions of stromal cells from the base of the polyp mass, a typical feature of hamartoma (FIG. 1L).

Example 2

PTEN Controls Cell Cycle in Intestinal Crypts

PTEN is known to inhibit cell proliferation through suppression of PI3K/Akt activity. Therefore, the proliferation state of cells in the intestinal polyp regions of the PTEN mutants was assessed by labeling actively cycling cells with a 3-hour pulse of BrdU. In normal/wild type (wt) crypts, BrdU$^+$ cells were limited to a narrow proliferation zone, the TAC, (FIG. 1I). In PTEN mutant polyps, however, the BrdU$^+$ cells were spread widely within the multiple crypt-like structures (FIG. 1J), the proliferating tissue appeared hyperplastic compared to the linear arrangement of proliferating cells in normal crypts (FIG. 1K), and the proliferative index of the epithelial cells (BrdU$^+$/(BrdU$^+$+BrdU$^-$)) was substantially increased (2.7 fold, P<0.01) compared to wt control (FIG. 1G).

Figure 2:
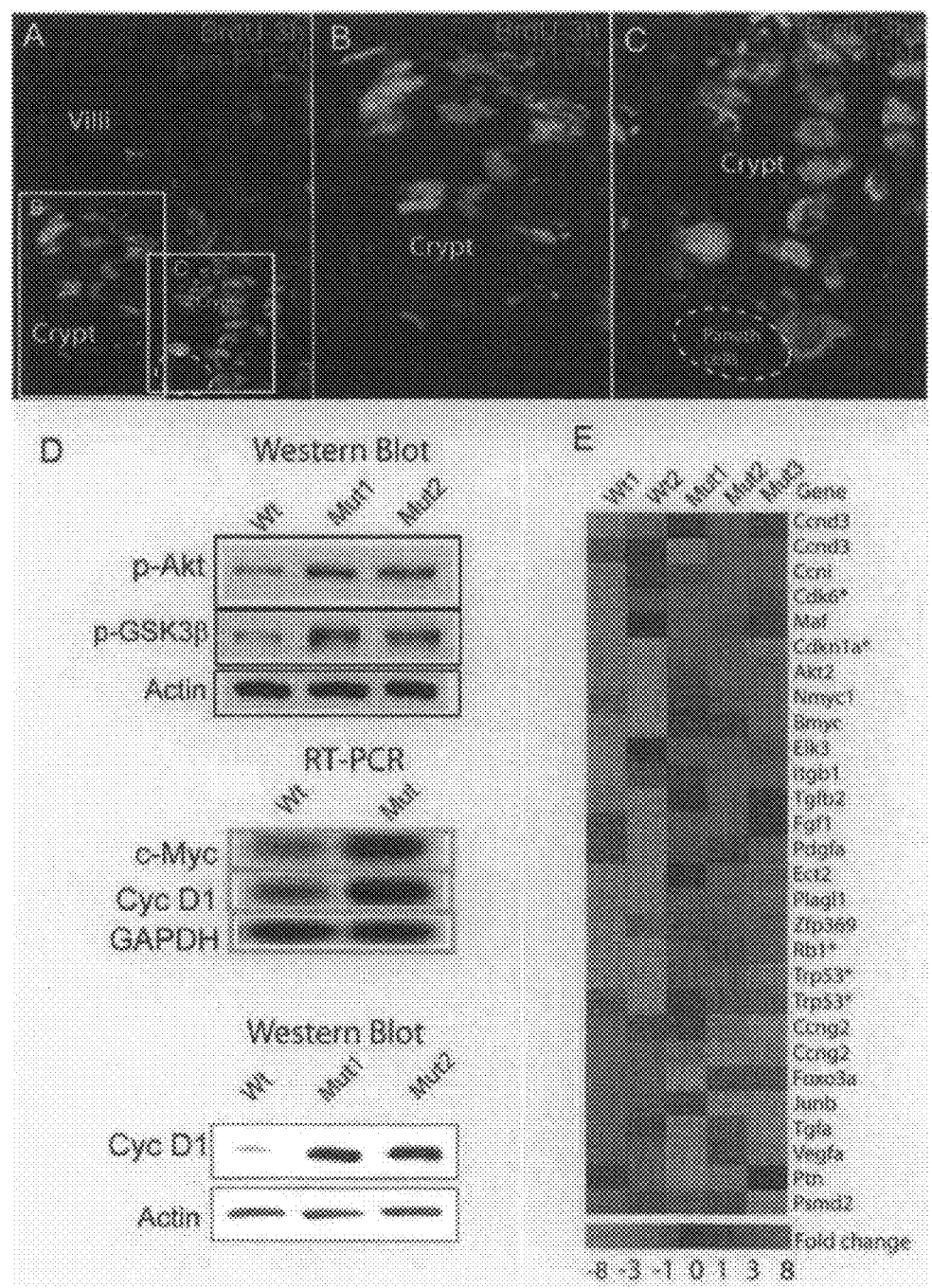
FIG. 2 shows PTEN expression in the intestine and the impact of PTEN inactivation on the activity of the PI3K-Akt pathway and on the expression of cell cycle regulators. Dual immuno-fluorescence using a pan-PTEN antibody to detect both p-PTEN and non-p-PTEN and an anti-BrdU antibody to detect pulse labeled cells (FIG. 2A). PTEN protein is detected in portions of the transit amplification compartment that are not actively cycling (FIG. 2B) and is also highly expressed in the ISC position (FIG. 2C).

Next, the relationship between PTEN expression and cell cycle status was examined. PTEN can be phosphorylated at its carboxy terminus by casein kinase II, which impairs its ability to be recruited to the plasma membrane to antagonize PI(3)K-Akt activity. The most active forms of PTEN are therefore non-phosphorylated but may be detected by a phosphorylation-insensitive antibody (pan-PTEN). Here, pan-PTEN immunostaining was found in two distinct cell populations. Multiple pan-PTEN positive cells were present in the portion of TAC in crypt, the majority of which are BrdU$^-$ (FIG. 2A,B). pan-PTEN$^+$, BrdU$^-$ cells was also observed towards the base of the crypt in the expected location of ISCs (FIG. 2A,C). PTEN expression in the less actively proliferating cells of the crypt, together with an increase in the proportion of proliferating cells in the PTEN mutant, suggests that PTEN acts in the TAC as a negative regulator of cell cycle.

In the PTEN mutants, deletion of the region encoding the phosphatase motif inactivates PTEN and is expected to result in activation of Akt (as measured by the phospho-form of Akt-T$^{473}$ or p-Akt hereafter) and phosphorylation of the Akt downstream target GSK3β at Ser$^9$ (p-GSK3β). Indeed, Western blot analysis demonstrated increased levels of p-Akt and p-GSK3β in the PTEN mutant mice (FIG. 2D, top panel). Cyclin D1, a known downstream target of the PI3K-Akt pathway is the regulatory subunit of a holoenzyme important for G$_1$/S phase transition. Elevated levels of Cyclin D1 mRNA and correspondingly elevated levels of Cyclin D1 protein (FIG. 2D, middle and lower panels) were found in intestine from PTEN-deficient mice as compared to controls. The ~2-3 fold increase in the number of highly Cyclin D1 positive ISCs in a limited proportion of the crypts and polyps was not sufficient to account for the 5-fold increase in Cyclin D1 protein levels (discussed below). PTEN mutants were also found to have elevated mRNA levels of proto-oncogene Myc (c-Myc) (FIG. 2D, middle panel), another downstream target of the PI(3)K-Akt pathway that promotes progression through G$_1$. Microarray analysis was performed to profile changes in expression (>two-fold) between PTEN mutant polyp regions and control intestine and identified up-regulated or down-regulated genes with the ontology term "regulation of cell cycle" (FIG. 2E). Since earlier results showed that Cyclin D1 was up-regulated, it was of interest that the array identified up-regulation of CyclinD3 (Ccnd3) and Cdk6, a CyclinD interacting factor. It is also notable that PTEN-loss resulted in higher levels of expression for key genes involved in the cell cycle G1/S checkpoint (shown by * in FIG. 2E) such as Rb1, Trp53 (p53), Cdk6 and Cdkn1a (Cdk inhibitor p21cip). Cdkn1a and the p53 co-factor, Plagl1, two of the up-regulated genes that inhibit cell cycle progression, are both positively regulated by p53. Up-regulation of both Itgb1 (β1-integrin) and Akt2 is suggestive of changes in the pathway linking integrin-mediated adhesion to Akt. Down-regulation of JunB in PTEN mutants is also intriguing; phenotypic similarity between PTEN and JunB mutants in hematopoetic stem cells also suggests a functional link between these genes.

In summary, increased proliferation rate in the polyps of PTEN mutants is attributable to a requirement for PTEN as a negative cell cycle regulator within the TAC of the crypt. Loss of PTEN results in increased Akt activity and increased expression of Cyclin D1 and Myc. Additional cell cycle regulators identified as candidates for control by the PTEN/Akt pathway in the intestine include CyclinD3, CyclinG2, N-Myc, B-Myc and multiple G1/S checkpoint genes.

Example 3

Musashi Positive Stem/Progenitor Cells Initiate Polyp Formation

Figure 3:
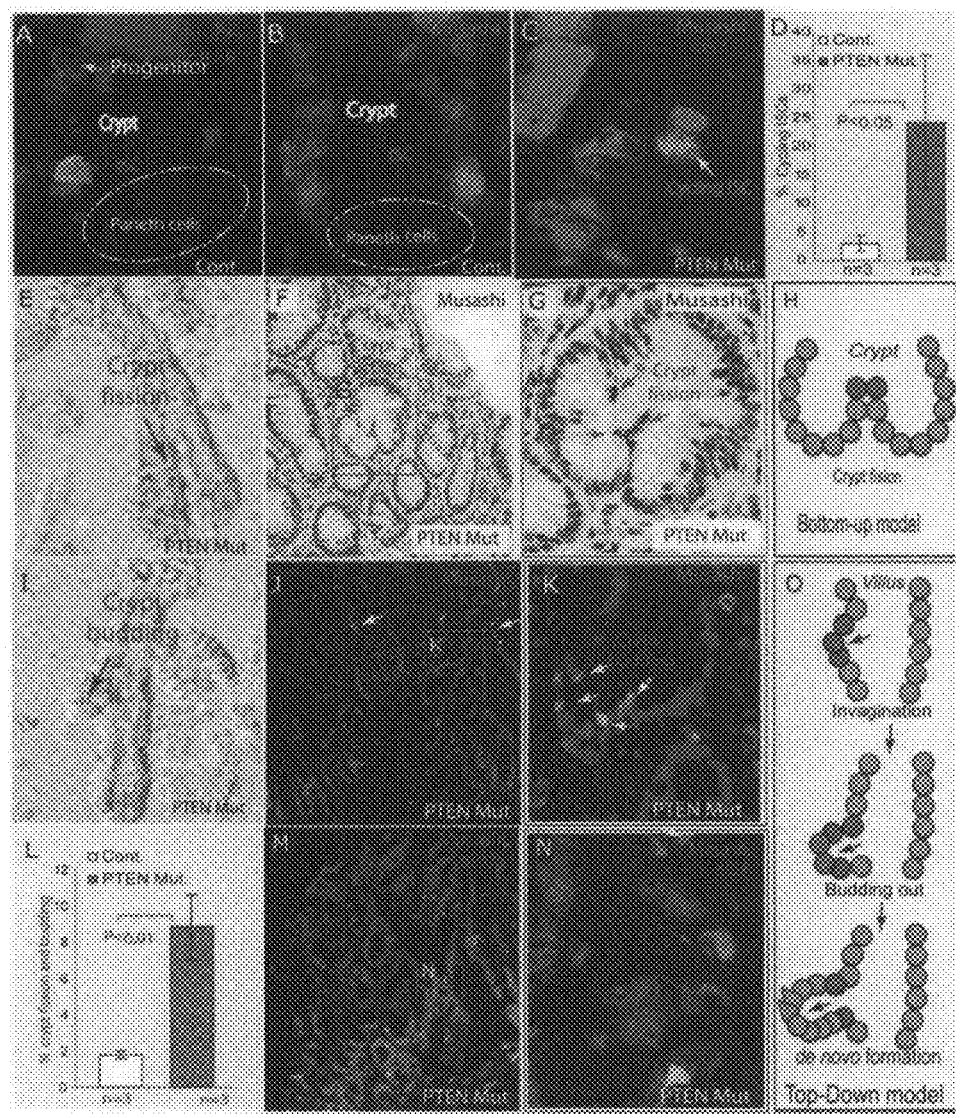
FIG. 3 shows PTEN-deficient intestinal stem cells were found at the point of initiation of crypt budding or crypt fission. Association of Musashi1, an ISC marker, with BrdU-LTR (long-term retention) in control cells are shown in FIG. 3A. Musashi1 was also expressed in progenitor cells in the mid crypt and was occasionally observed in the transition region between crypt and villus (see also FIG. 8). In control cells, ISCs, identified as Musashi1$^+$ cells positioned near Paneth cells, are in most cases Ki67$^{-ve}$ and therefore in a slow-cycling state (FIG. 3B). Association of Musashi1, an ISC marker, with BrdU-LTR (long-term retention) in PTEN mutant intestine cells are shown in FIG. 3C. Comparison of the percentage of double positive (Musashi1$^+$, Ki67$^+$) cells in control and PTEN mutant intestine is shown in FIG. 3D.
Figure 8:
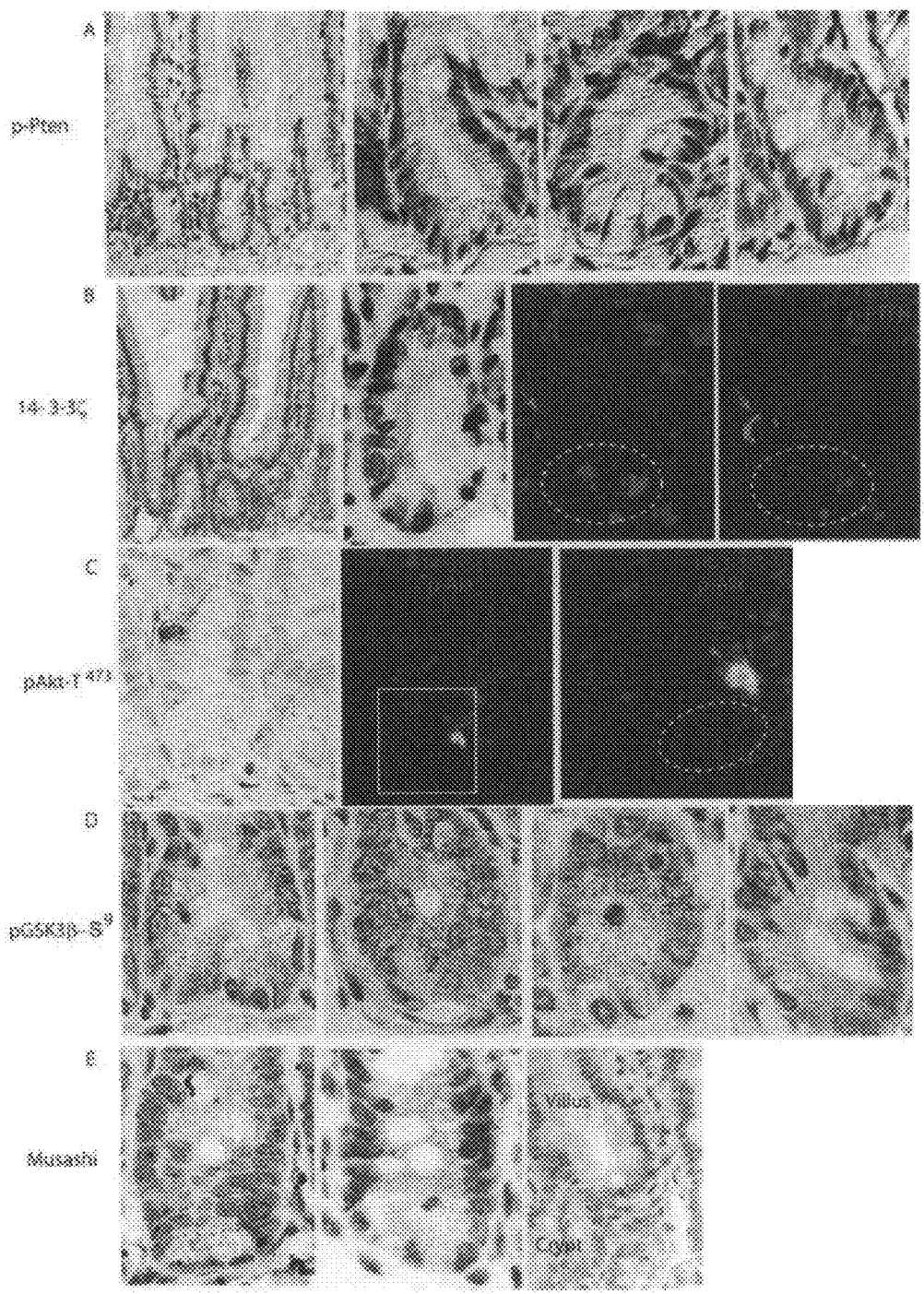
FIG. 8 is a comparison of expression patterns of p-PTEN (FIG. 8A), p-Akt (FIG. 8C), 14-3-3ζ (FIG. 8B) pGSK3β (FIG. 8D), and Musashi (FIG. 8E). Compare the staining pattern of Musashi using anti-Musashi antibody clone 14H1 to the pattern in FIGS. 10A, 10B.
Figure 10:
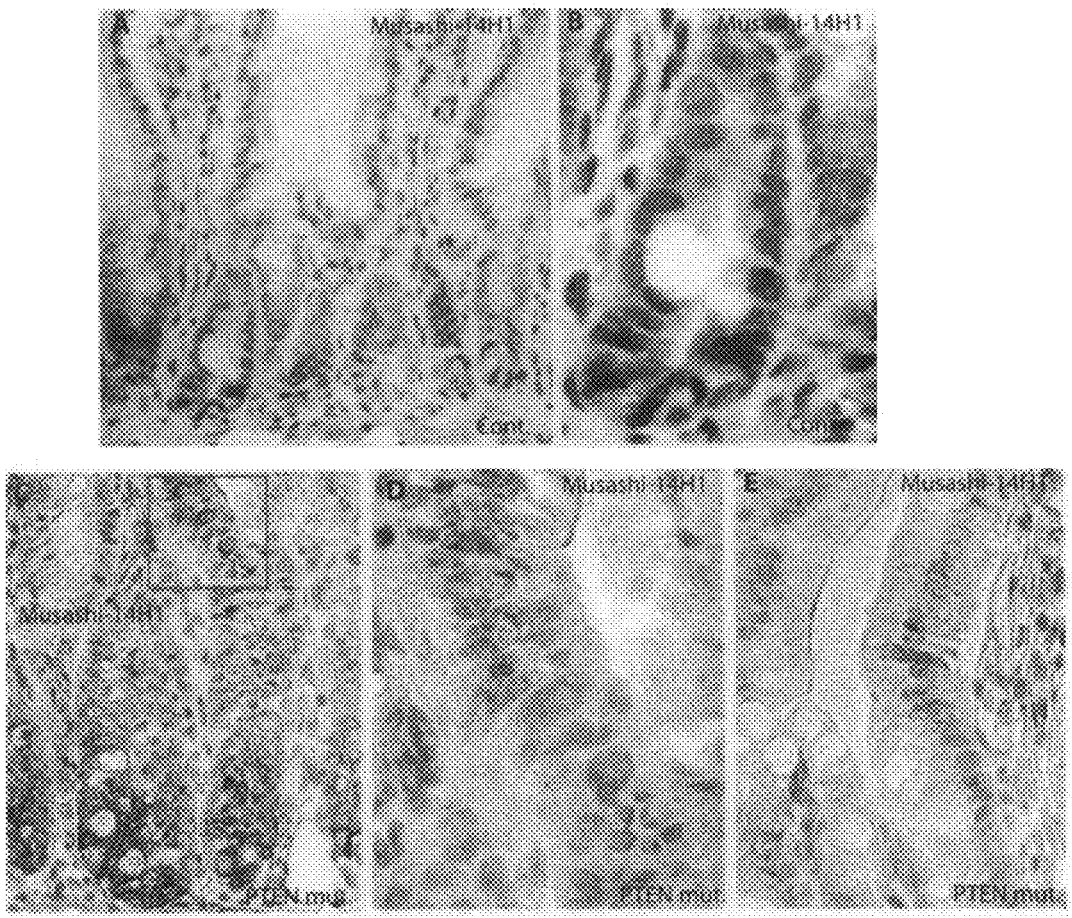
FIG. 10 shows detection of Musashi1 expression using anti-Musashi antibody clone (14H1) (Potten & Okano, Differentiation 2003).

The observations that PTEN is expressed in ISCs (FIG. 2C) and that PTEN loss results in polyposis raise the possibility that PTEN-deficient ISCs are responsible for the polyp formation. The ISC marker Musashi (Musashi1) was used to test this hypothesis. In normal intestinal crypts two classes of Musashi$^+$ cells were detected by a polyclonal anti-Musashi1 antibody (Chemicon; Cat # AB5977). As expected, many Musashi$^+$ crypt cells were detected at the ISC position and could be co-stained for long-term-retention of BrdU (BrdU-LTR) (FIG. 3A), but some isolated Musashi$^+$BrdU-LTR$^-$ cells (potentially progenitor cells) were observed higher in the crypt (FIG. 3A) and in the transition zone between crypt and villus (FIG. 8E). A rat monoclonal anti-Musashi1 antibody yielded a somewhat broader pattern of signal but had a similar distribution of strongly positive cells (Potten et al., 2003; FIG. 10). The differential ability of the Musashi$^+$ ISCs and putative progenitors to retain BrdU over long periods suggests that the ISCs are more frequently in a prolonged quiescent state. Nevertheless, Musashi$^+$ 'progenitors' shared multiple molecular characteristics with ISCs (see below; FIG. 8), These Musashi$^+$ 'progenitors' are discussed herein together as "Musashi$^+$ ISCs/progenitors" (hereafter M$^+$ISC/p). To support ongoing intestinal regeneration ISCs need to be able to transition between the quiescent state and active state where they can undergo division. PTEN-deficient M$^+$ISC/p cycle were found far more often than their normal counterparts. In normal intestine only around 2-4% of the M$^+$ISC/p were labeled by Ki67, a proliferating cell marker, suggesting that vast majority are either quiescent or slow cycling (FIG. 3B, D). In the polyps of PTEN mutants, however, an average of 24% of the M$^+$ISC/p were double positive for Musashi and Ki67 (FIG. 3C, D). The marked increase in active cycling in this population mirrors the change in proliferation rate observed in the rest of the mutant intestinal epithelium and may reflect an increased rate of cell cycle entry, more rapid progression, or both.

Crypt expansion in polyposis can be caused by 'bottom-up' crypt fission (division of an existing crypt starting at its base), or by 'top-down' de novo crypt formation (budding of a new crypt from a crypt or villus). Both crypt fission and de novo crypt formation are also frequently seen in polyposis. Both these mechanisms of crypt expansion were operative in PTEN mutant intestines, and both were associated with an excessive production of M$^+$/ISPs (FIG. 3E-3O).

Figure 9:
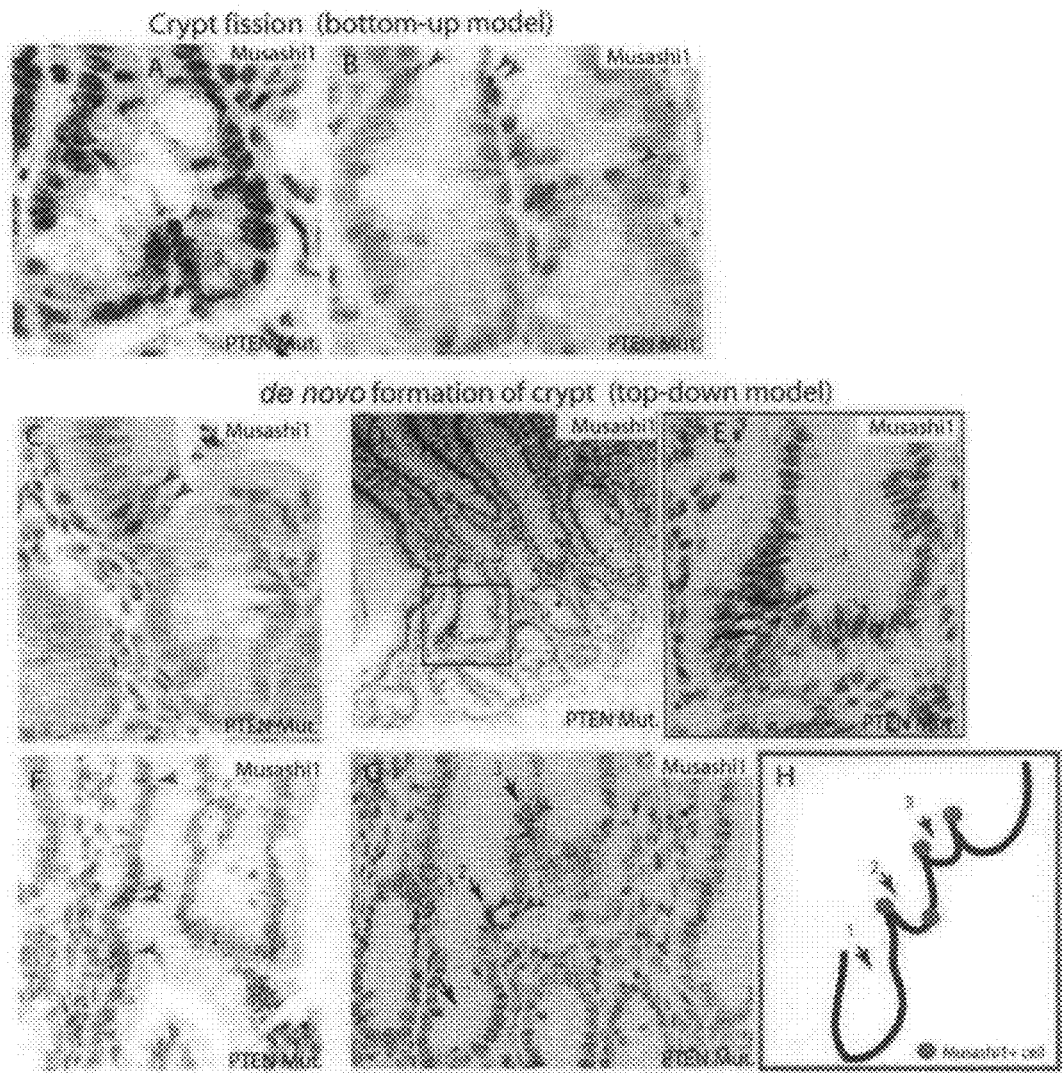
FIG. 9 shows a cluster of Musashi+ cells that were detected at the initiation site of crypt budding or crypt fission of PTEN mutants.

Dissociation of PTEN mutant polyps revealed that crypts were undergoing fission (FIG. 3E) or budding (FIG. 3I) at a significantly higher rate than in controls (FIG. 3L). M$^+$ISC/p, a rare population in normal intestine (FIG. 8E), still formed only a minor component of the PTEN mutant polyps but were found in clusters that appeared to be seeding the formation of new crypts. In examples of crypt fission, M$^+$ISC/p cells were observed to be forming the apex of the ridge between crypts, suggesting that M$^+$ISC/p cells are central to the fission process (FIG. 3F-3H; FIG. 9A-9B). In the de novo formation of crypt-like structures in either crypts or villi (crypt budding), small branches were found in the polyps (newly forming crypts, FIG. 3J, 3K, 3M, 3N; FIGS. 9C-9E) contained pairs or small groups of M$^+$ISC/p cells along with other cycling and non-cycling cells, suggesting stem cell-directed growth (FIG. 3K, 3N, 3O). Sequential formation of new polyps was also observed along the edge of villi and groups of Musashi$^+$ cells among epithelial cells in villi (FIG. 3J, FIGS. 9F-9H) where invagination is being initiated (white arrows in FIG. 3J). Hence, in both the crypt fission and crypt budding, Musashi$^+$ cells were found at the initiation center of newly formed crypts (FIG. 3H, 3O).

Example 4

PTEN/Akt Pathway Activity is Linked to ISC/Progenitor Cell Number and Behavior

The link between loss of PTEN and a change in ISC/progenitor behavior was next examined by investigating the expression/activity of molecules known to be downstream of PTEN/Akt, focusing on the pathways leading to β-catenin-dependent transcription (FIG. 4U) and cell cycle entry and progression (FIG. 4V).

Figure 4:
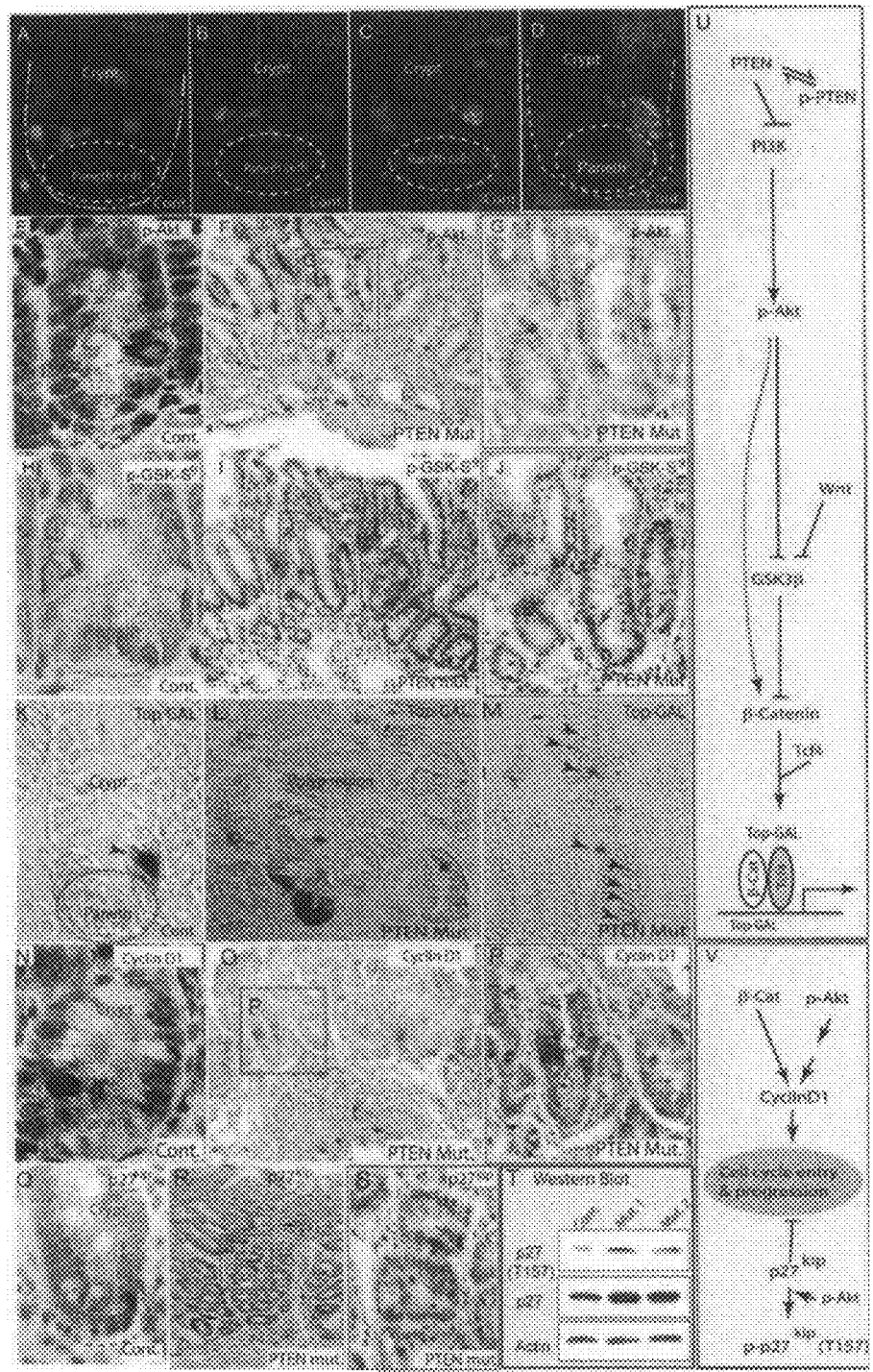
FIG. 4 shows the association of the PTEN-Akt pathway with ISCs and analysis of the activation of the PI3K-Akt pathway upon PTEN inactivation.

First, the relationship between the M$^+$ISC/p population and the cells with active Akt signaling was established. The inventors have previously shown that the presence of the phosphorylated form of PTEN (p-PTEN) and active Akt signaling (pAkt) are both commonly associated with BrdU-LTR, a property of ISCs. The adaptor protein 14-3-3ζ, which binds β-catenin and participates in its Akt-dependent activation, exhibits a similar distribution pattern. A more detailed analysis found that cells in the ISC position towards the base of the crypt were highly positive for p-PTEN, p-Akt, p-GSK3β, 14-3-3-ζ, and Musashi (FIG. 4A, 4B, 4C, 4H; FIG. 8). Lower levels of p-Akt and p-GSK3β signal were observed in the adjacent TAC (FIG. 4 E, H). As was observed with Musashi, a limited number of progenitor cells higher in the crypt were highly positive for the Akt pathway markers (FIG. 8). These data strongly suggesting that in normal intestine, a proportion of M$^+$ISC/p have high activity of Akt and correspondingly high levels of p-GSK3β. Similar co-localization studies established that ISC with a high activity of Akt (p-Akt$^+$ or p-PTEN$^+$) were commonly strongly positive for nuclear cyclinD1 and nuclear, or nuclear plus cytoplasmic, p27$^{Kip1}$ (FIG. 4C, 4D).

In PTEN mutant polyps, an abnormally increased proportion of cells were intensely positive for p-Akt (FIG. 4F, 4G) and p-GSK3β (FIG. 4I, 4J) and such cells were found at quite different levels within the same crypt or in unusual clusters (arrows in FIG. 4G, J). The distribution patterns of cells highly positive for p-GSK3β or p-Akt (FIG. 4G, 4J) were very similar, consistent with Akt phosphorylation of its target GSK3β. Thus, loss of PTEN function increases the number and alters the distribution of ISCs/progenitors engaged in active Akt signaling.

Figure 11:
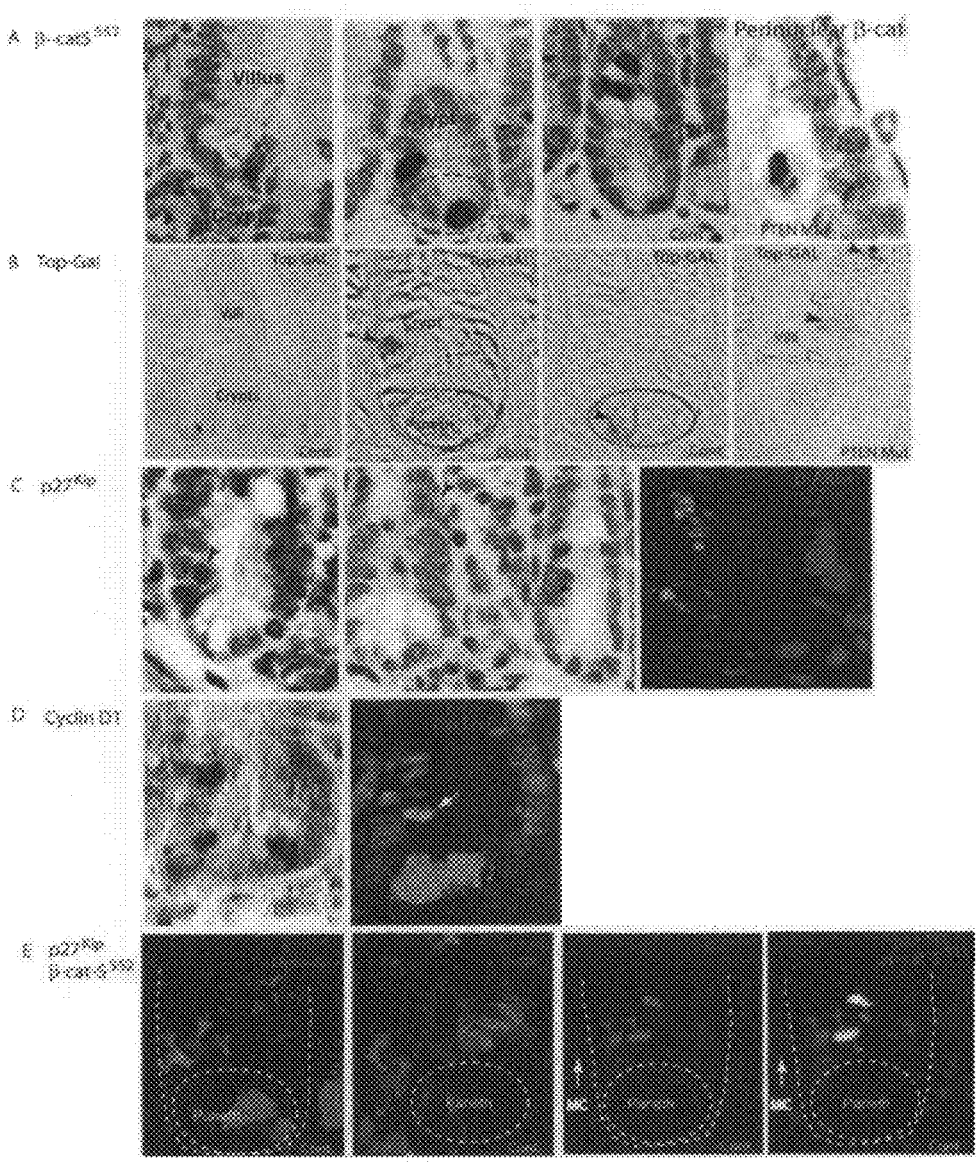
FIG. 11 compares expression patterns of β-cat-p-$S^{552}$, Top-Gal, $P27^{kip1}$, and Cyclin D1.

Phosphorylation of GSK3β by Akt may assist the Wnt signal in inactivating GSK3β, thereby preventing the proteasome-mediated degradation of β-catenin and facilitating its nuclear translocation and transcription regulation. Functional changes in β-catenin-mediated transcriptional activity were assessed using the transgenic reporter Top-Gal, in which β-catenin and TCFs co-operatively drive β-galactosidase expression (FIG. 4U). In PTEN mutants, the number of Top-Gal$^+$ cells was increased and Top-Gal expression, normally a property of ISCs or Paneth cells, was ectopically detected in the villi (FIG. 4L-4M; FIG. 11B).

One mechanisms by which Akt might promote M+ISC/p proliferation is the up-regulation of Cyclin D1, a consequence of Akt acting through mTor or via enhanced β-catenin activity. Another possible mechanism is the inactivation of cycle dependent kinase inhibitor Cdkn1b (p27$^{kip1}$), since phosphorylation of p27$^{kip1}$ by Akt at threonine 157 induces its nuclear export (FIG. 4V).

In normal intestine high levels of nuclear-localized Cyclin D1 are detected in the slow cycling (Ki67 negative) population of M+ISC/p; whereas, lower levels of Cyclin D1 are found in the TAC (FIG. 4D, 4N; FIG. 11D). Polyps in PTEN mutants contained an abnormally high number and disorganized clustered arrangement of cells with high levels of nuclear Cyclin D1 (FIGS. 4O, 4P), consistent with the observed increased numbers and altered distribution of cells with active Akt signaling and β-catenin-mediated transcriptional activity. Paralleling these changes the polyps of PTEN mutants frequently contained increased numbers of cells with high levels of nuclear p27$^{kip1}$ (FIGS. 4Q-4S). Due to the limited performance of available antibodies, the T$^{157}$ phosphorylation status of p27$^{kip1}$ on tissue sections was not determined, but western blot analysis showed that PTEN-deficiency in the intestine resulted in increased overall levels of both p27$^{kip1}$ and T$^{157}$-phosphorylated p27$^{kip1}$ (FIG. 4T). Together, these results are consistent with the loss of PTEN increasing the numbers of stem and progenitor cells, increasing the proportion of such cells that have high levels of nuclear Cyclin D1 and/or nuclear p27$^{kip1}$, or affecting both the number and cell cycle status of this cell population.

Example 5

Akt Phosphorylates the C-Terminus of β-Catenin at Ser$^{552}$

In a variety of systems, including the intestine, nuclear localization of β-catenin is believed to be a key event in stem cell activation. Thus definition of the interaction between the PTEN/Akt pathway and β-catenin nuclear localization was sought. Previously the inventors proposed that Akt co-ordinates with Wnt signaling and assists in the activation of β-catenin in ISCs. There are two routes by which Akt, a basophilic serine/threonine kinase, may promote β-catenin activation (nuclear localization): indirectly through phosphorylation of GSK3β or directly by phosphorylation of β-catenin itself. The phosphorylation of GSK3β by Akt may increase the stability of p-catenin by impairing its ubiquitin-mediated degradation, whereas the direct phosphorylation of β-catenin by Akt can prime β-catenin for 14-3-3ζ binding and further stabilization.

Figure 5:
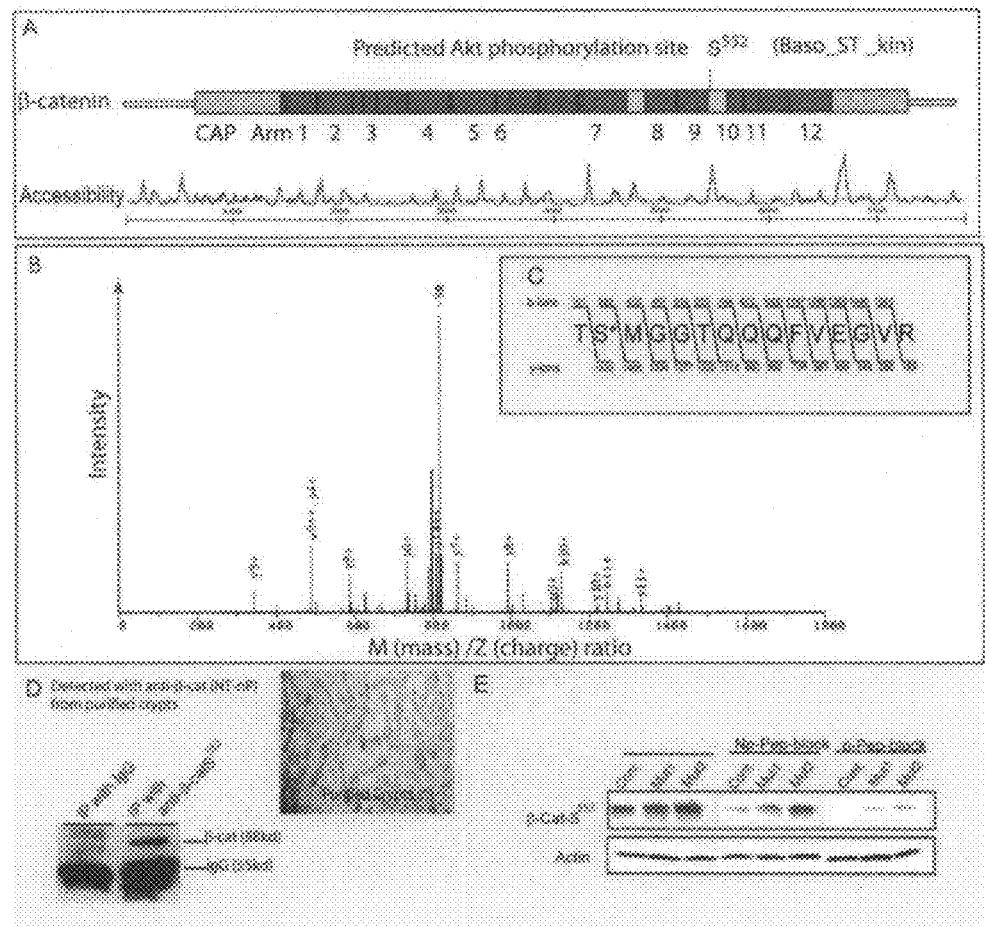
FIG. 5 illustrates identification of the Akt phosphorylation site at the C-terminus of a murine β-catenin polypeptide.

Bioinformatic analysis (FIG. 5A) revealed a putative Akt phosphorylation site at Ser$^{552}$ which was confirmed by mass-spectrometry (FIG. 5B, 5C). Lower-stringency searches identified additional putative Akt sites at T217, T332 and S675. Akt was used to phosphorylate purified β-catenin protein in vitro, then the phosphorylated protein was subjected to trypsin digestion, phosphopeptide isolation, and liquid chromatography-mass-spectrometry. The collision induced dissociation spectrum for the peptide spanning Ser$^{552}$ (FIG. 5B) showed a major peak representing the loss of the 98 Da. H$_3$PO$_4$ group from the parent ion, indicating that this peptide (shown in FIG. 5C) is phosphorylated by Akt. Consistent with the known impact of Akt on 14-3-3ζ binding to β-catenin, the RRTS sequence containing Ser$^{552}$ forms a phospho-serine motif that serves as an optimal recognition site for 14-3-3ζ

To assay for β-catenin phosphorylated by Akt at Ser$^{552}$, a phospho-specific antibody (anti-p-beta-cat-Ser552 antibody) was developed and characterized. In immunoprecipitation experiments (FIG. 5D), performed with purified intestinal crypts (see inset), the anti-p-beta-cat-Ser552 antibody pulled down forms of β-catenin that could be recognized by an existing antibody recognizing N-terminal non-phosphorylated (NT-nP) β-catenin, which is typically enriched in the nucleus. As well as indicating the specificity of this antibody for β-catenin, this result suggests that the forms of β-catenin in intestinal crypts include a population of molecules that are phosphorylated on Ser$^{552}$ but non-phosphorylated at the N-terminus. By western blot this antibody appropriately detected β-catenin and efficient blocking of the signal was achieved when the antibody was pre-incubated with a phospho-peptide for the antigen, but not when the equivalent non-phospho peptide was used, indicating that the antibody is phospho-specific (FIG. 5E). Use of this antibody revealed that polyps of PTEN mutants had elevated levels of β-catenin phosphorylated at Ser$^{552}$ (β-cat-p-S$^{552}$) when compared with control intestine (FIG. 5E).

Example 6

β-Catenin Phosphorylated at Ser552 is Localized in the Nucleus of ISCs

Figure 6:
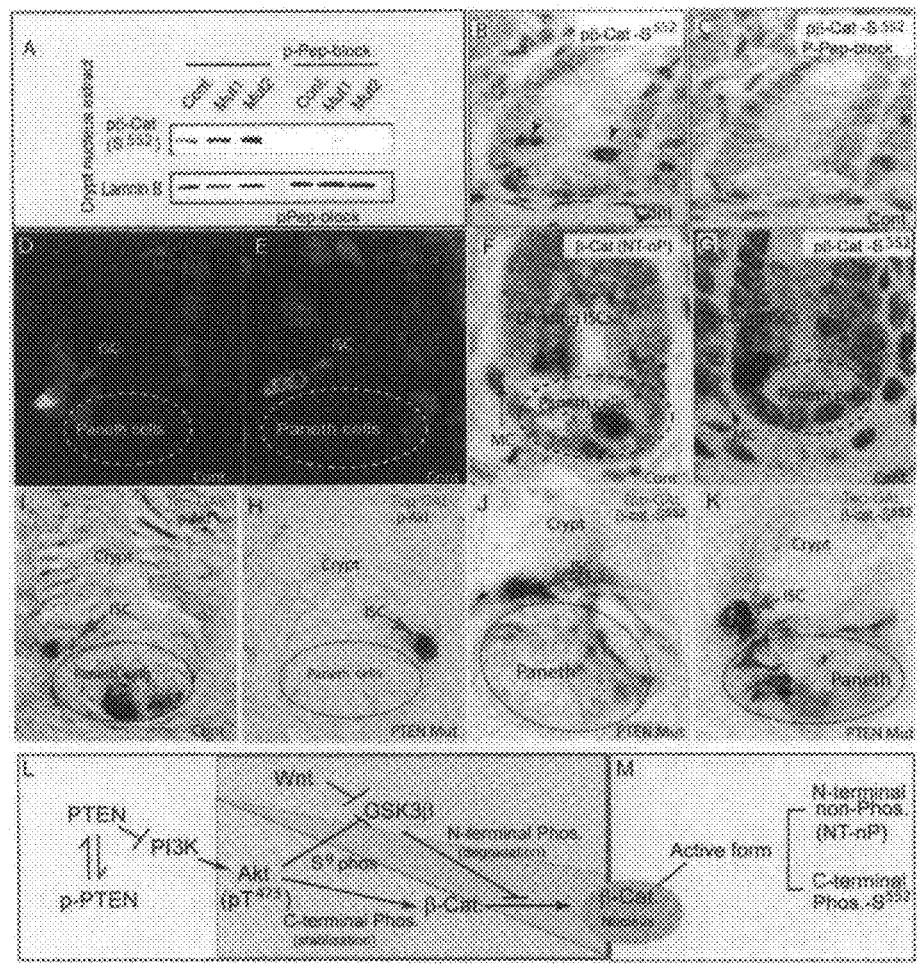
FIG. 6 shows that Akt activity coincides with the nuclear form of β-cat-p-S552 and β-catenin-dependent transcriptional activity in ISCs. Western blot analyses comparing the levels of nuclear β-cat-p-S$^{552}$ protein in crypt nuclear extract between Control and PTEN mutant intestines (FIG. 6A). p-Pep-blocker was able to specifically inhibit binding of β-catenin by anti-p-beta-cat-Ser552 antibody. Cells at the stem cell position have nuclear β-cat-p-S$^{552}$ (FIG. 6B). Signal detected by anti-p-beta-cat-Ser552 antibody can be blocked by p-Pep-blocker (FIG. 6C).

Using the phospho-specific antibody, the relationship between Ser$^{552}$ phosphorylation and β-catenin nuclear localization and activity was examined. Western blots performed on nuclear extracts of intestinal crypts indicated that β-cat-p-S552 was present in the nucleus, with higher levels of protein detected in PTEN mutants than in controls (FIG. 6A). Immunohistochemistry revealed a strong spatial and sub-cellular localization of anti-β-cat-p-S552 signal with intense nuclear signal being present in ISC/s progenitors and occasionally also in Paneth cells (FIG. 6B; FIG. 11A). This signal could be blocking with the antigen peptide, confirming the specificity of the staining (FIG. 6C). Cells with lower level signal in a peri-nuclear pattern were also observed in some crypt cells (FIG. 11A).

Consistent with the immunoprecipitation experiments, the NT-np and β-cat-p-S$^{552}$ forms of β-catenin exhibited similar distributions in intestinal crypts. Active (NT-np) β-catenin was observed in the nuclei of M+ISCs (FIG. 6D), in dividing ISCs (FIG. 6F), and in a subset of cells in other crypt positions (for example, in the Paneth cell shown in FIG. 6F). The antibody for the β-cat-p-S$^{552}$ form likewise detected nuclear β-catenin in a pattern substantially consisting of Ki67$^{-ve}$ ISCs (FIG. 6E) and dividing ISCs (FIG. 6G), but also including cells at other crypt positions (FIG. 11A). Irrespective of the antibody used, ISCs with nuclear β-catenin were observed to undergo division perpendicular to the plane of the epithelium (a feature of asymmetric division) and in close proximity to a mesenchymal cell (MC, a putative stem cell niche) (FIGS. 6F, 6G). In pairs of asymmetrically dividing or recently divided ISCs (based on the expression of Musashi or nuclear p27$^{kip1}$ and on relative position) both cells were usually positive for nuclear β-cat-p-S552, but pairs of nuclear p27$^{kip1}$ positive cells were also occasionally observed in which only the cell distal to the MC had nuclear anti-β-cat-p-S552 signal (FIG. 11E). Use of alternative β-catenin antibodies in co-staining experiments revealed that ISCs could also have a membrane or cytoplasmic, rather than nuclear, distribution of β-catenin (FIG. 11E).

For cells in the ISC position, but not for Paneth cells, there was a strong correlation between Top-Gal expression and either Akt activity (FIGS. 6H, 6I) or β-cat-p-S552 nuclear localization (FIGS. 6J, 6K). This correlation was most readily apparent in PTEN mutants where ISCs are more frequently positive for p-Akt, β-cat-p-S552 or Top-Gal activity. Based on the biochemical and immunostaining data, a molecular pathway is proposed by which the Wnt and PTEN/Akt pathways interact to control β-catenin nuclear localization and transcriptional activity in the M+ISC/p (FIG. 6L). In these cells β-catenin exists in a range of states, and the nuclear forms may be expected to lack phosphorylation at the N terminus, to be phosphorylated towards the C terminus by Akt, or to have both these properties (FIG. 6M).

Example 7

Cells with Nuclear B-Cat-P-$S^{552}$ Initiate Crypt Fission and Budding

Figure 7:
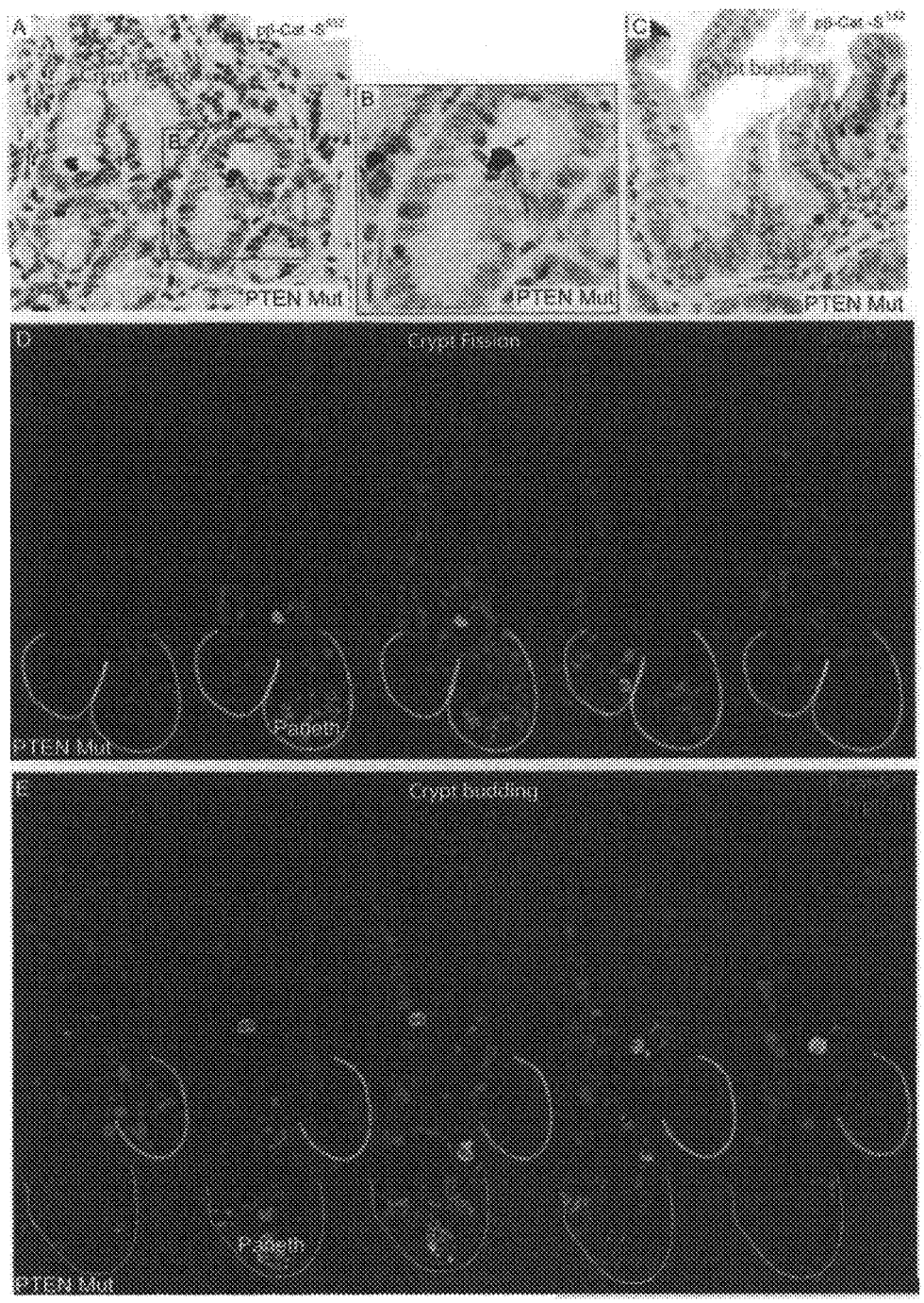
FIG. 7 shows detection of cells with nuclear β-cat-p-S$^{552}$ in PTEN mutants. In PTEN mutant polyps, clusters of cells with nuclear β-cat-p-S$^{552}$ are found at the apex of the ridge of dividing crypts in crypt fission (FIGS. 7A, 7B) and at the point of initiation of budding crypts (FIG. 7C).
Figure 12:
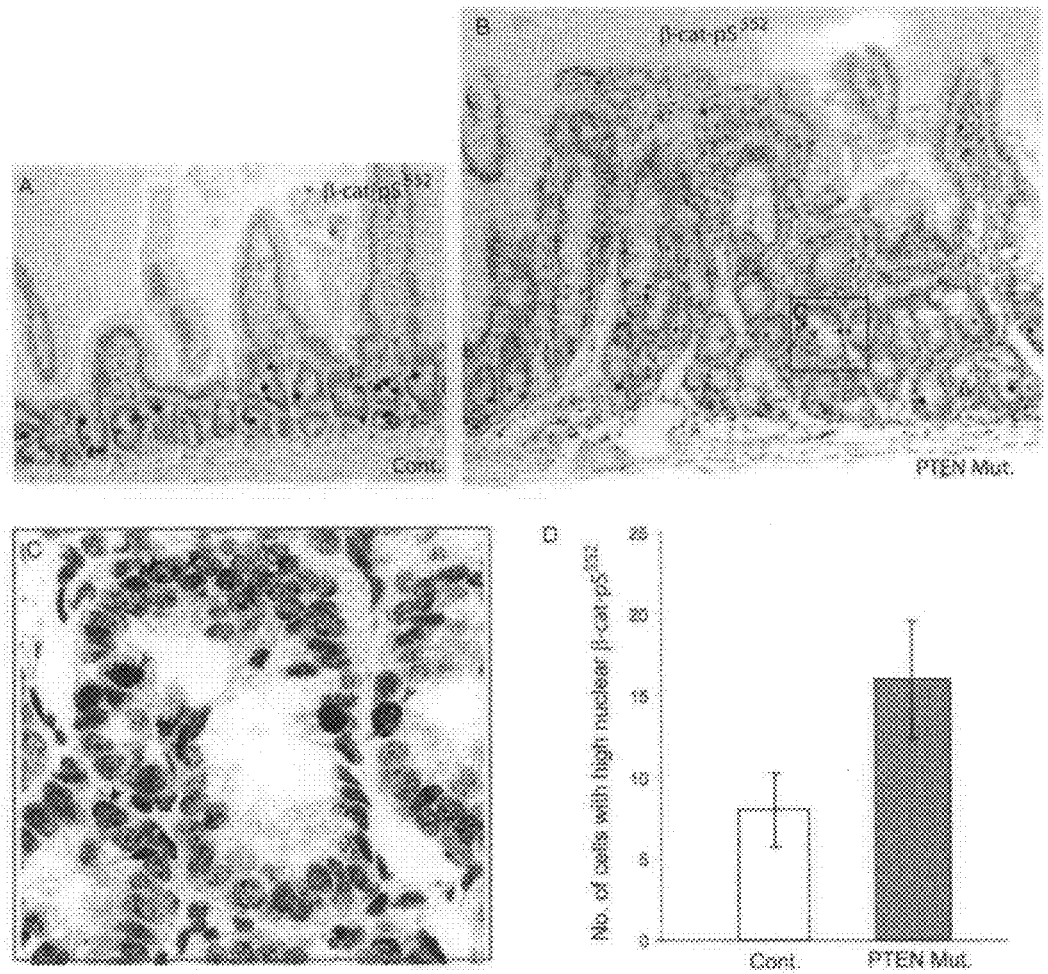
FIG. 12 illustrates the distribution of cells with β-cat-p-$S^{552}$.

In PTEN mutant polyps, cells with nuclear anti-β-cat-p-$S^{552}$ signal were increased in number and abnormally localized (FIG. 7, FIG. 12), similar to the findings described above with Musashi and with markers of an active Akt pathway. Per unit length of intestine the PTEN mutant polyps contained twice as many cells with nuclear anti-β-cat-p-$S^{552}$ signal as control intestines (FIGS. 12A, 12B, 12D). PTEN loss has less effect on the number of such cells per crypt, suggesting that the overall increase is correlated with the increased number of crypts per unit length in the mutants. Consistent with this relationship, in PTEN mutant the cells with nuclear β-cat-p-$S^{552}$ were frequently clustered together and were found at sites of crypt fission (FIG. 7A, 7B) and at sites of invagination where new crypts were budding from the sides of villi or crypts (FIG. 7C). Since fission and budding can be difficult to recognize from sections, examples of crypt fission or budding were isolated from the mutant polyps, and then immunofluorescence and confocal microscopy were used to identify cells with nuclear β-cat-p-$Ser^{552}$. Cells with nuclear β-cat-p-$S^{552}$ were found localized at the apex of the ridge dividing the crypts in crypt fission (red arrowhead in FIG. 7D) and were present at the junction between newly budding crypts and their parent crypts (red arrowhead in FIG. 7E).

Example 8

Detection of Polyp Forming Stem Cells

It is envisioned that the relationship between $Ser^{552}$ phosphorylation, β-catenin nuclear localization, and polyp formation by putative cancer stem cells may be further elucidated by using the described phospho-specific antibody in combination with one or more antibodies that are specific for phospho-β-catenin, wherein the β-catenin is phosphorylated at $Ser^{552}$ and at one or more positions (i.e. T217, T332, S673, or a second site of the R10 Armadillo repeat of β-catenin). These additional antibodies may be specific for only one of the additional phosphorylation sites or recognize $Ser^{552}$ and a second site of phosphorylation.

Examination of the relationships and polyp formation will be conducted using methods similar to those described above. Specifically, antibodies will be prepared using the same methodology with the exception that the phospho-β-catenin will be phosphorylated at one or more of the previously identified sites. Detection of specific binding will be as described above using similar parameters to exclude false positives and overlap.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

CITED DOCUMENTS

The following documents, as well as those cited within this specification, are specifically incorporated by reference to the extent that they provide or teach exemplary methodology, techniques and/or compositions supplemental to those employed herein.

Aberle, H., Bauer, A., Stappert, J., Kispert, A. & Kemler, R. beta-catenin is a target for the ubiquitin-proteasome pathway. EMBO J. 16, 3797-3804 (1997).

Akashi, K. et al. Transcriptional accessibility for genes of multiple tissues and hematopoietic lineages is hierarchically controlled during early hematopoiesis. Blood 101, 383-389 (2003).

Al-Hajj, M., Wicha, M. S., Benito-Hernandez, A., Morrison, S. J. & Clarke, M. F. Prospective identification of tumorigenic breast cancer cells. Proc. Natl. Acad. Sci. U.S.A. 100, 3983-3988 (2003).

Altschul et al. J. Mol. Biol. 215: 403-410. (1990).

Altschul et al. Nucleic Acids Res. 25: 3389-3402. (1990).

Asai, R., Okano, H. & Yasugi, S. Correlation between Musashi-1 and c-hairy-1 expression and cell proliferation activity in the developing intestine and stomach of both chicken and mouse. Dev. Growth Differ. 47, 501-510 (2005).

Bei, M. and Maas, R. Development 125, 4325-4333 (1998).

Belletti, et al., J Biol Chem 276, 13867-13874 (2001).

Bitgood and McMahon. Dev Biol 172, 126-138 (1995).

Bjerknes, M. & Cheng, H. Clonal analysis of mouse intestinal epithelial progenitors. Gastroenterology 116, 7-14 (1999).

Booth and Potten. J Clin Invest 105, 1493-1499 (2000).

Brittan, M. & Wright, N. A. Gastrointestinal stem cells. J. Pathol. 197, 492-509 (2002).

Campbell, In: Monoclonal Antibody Technology, Laboratory Techniques in Biochemistry and Molecular Biology, Vol. 13, Burden and Von Knippenberg (Eds.), Elsevier, Amsterdam, pp. 75-83, 1984.

Clement, et al., J Cancer Res Clin Oncol 126, 271-279 (2000).

Cotran, et al., Sixth Edition of "Robinson Pathological Basis of Diseases" by WB Saunders Company Chapter 18, 828 (1999).

Cotsarelis, et al., Cell 61, 1329-1337 (1990).

Cully, M., You, H., Levine, A. J. & Mak, T. W. Beyond PTEN mutations: the PI3K pathway as an integrator of multiple inputs during tumorigenesis. Nat. Rev. Cancer 6, 184-192 (2006).

Dale and Wardle. *Semin Cell Dev Biol* 10, 319-26 (1999).

Datta, et al. *Cell* 91, 231-41 (1997).

Datta, S. R. et al. 14-3-3 proteins and survival kinases cooperate to inactivate BAD by BH3 domain phosphorylation. Mol. Cell. 6, 41-51 (2000).

Deng and Lin. *Dev Biol* 189, 79-94 (1997).

Entchev et al., *Cell* 103, 981-91 (2000).

Fero, et al., *Cell* 85, 733-44 (1996).

Fuchs, et al., Dev Cell 1, 13-25 (2001).
Fukumoto, et al., J Biol Chem 276, 17479-17483 (2001).
Gefter et al., "A simple method for polyethylene glycol-promoted hybridization of mouse myeloma cells, "Somatic Cell Genet., 3:231-236, 1977.
Gera, J. F. et al. AKT activity determines sensitivity to mammalian target of rapamycin (mTOR) inhibitors by regulating cyclin D1 and c-myc expression. J. Biol. Chem. 279, 2737-2746 (2004).
Ghosh-Choudhury, et al., J Biol Chem 277, 33361-33368 (2002).
Goding, In: Monoclonal Antibodies: Principles and Practice, 2$^{nd}$ Edition, Academic Press, Orlando, Fla., pp. 60-61, 65-66, 71-74, 1986.
Gottardi, C. J. & Gumbiner, B. M. Distinct molecular forms of beta-catenin are targeted to adhesive or transcriptional complexes. J. Cell Biol. 167, 339-349 (2004).
Greaves, L. C. et al. Mitochondrial DNA mutations are established in human colonic stem cells, and mutated clones expand by crypt fission. Proc. Natl. Acad. Sci. U.S.A. 103, 714-719 (2006).
Gregorieff, A. et al. Expression pattern of Wnt signaling components in the adult intestine. Gastroenterology 129, 626-638 (2005).
Grossmann, J. et al. New isolation technique to study apoptosis in human intestinal epithelial cells. Am. J. Pathol. 153, 53-62 (1998).
Groszer, M. et al. Negative regulation of neural stem/progenitor cell proliferation by the Pten tumor suppressor gene in vivo. Science 294, 2186-2189 (2001).
Groszer, M. et al. PTEN negatively regulates neural stem cell self-renewal by modulating G0-G1 cell cycle entry. Proc. Natl. Acad. Sci. U.S.A. 103, 111-116 (2006).
Guatelli et al. PNAS 87: 1874-1878 (1990).
Haramis, A. P. et al. De novo crypt formation and juvenile polyposis on BMP inhibition in mouse intestine. Science 303, 1684-1686 (2004).
Harlow and Lane. Antibodies: A Laboratory Manual, Cold Spring Harbor Laboratory, New York, 1988.
He, X. C. et al. BMP signaling inhibits intestinal stem cell self-renewal through suppression of Wnt-beta-catenin signaling. Nat. Genet. 36, 1117-1121 (2004).
Hefferan, et al. J Biol Chem 275, 20255-9 (2000).
Hermiston, M. L. & Gordon, J. I. Organization of the crypt-villus axis and evolution of its stem cell hierarchy during intestinal development. Am. J. Physiol. 268, G813-822 (1995).
Hogan. Curr Opin Genet Dev 6, 432-8 (1996).
Houlston, et al., Hum Mol Genet. 7, 1907-1912 (1998).
Howe, et al., Science 280, 1086-1088 (1998).
Howe, J. R. et al. Germline mutations of the gene encoding bone morphogenetic protein receptor 1A in juvenile polyposis. Nat. Genet. 28, 184-187 (2001).
Hu, et al., Development 128: 2373-2384 (2001).
Hu M, et al. Multilineage gene expression precedes commitment in the hemopoietic system. Genes Dev. 11: 774-785 (1997).
Huber, A. H., Nelson, W. J. & Weis, W. I. Three-Dimensional Structure of the Armadillo Repeat Region of [beta]-Catenin. Cell 90, 871-882 (1997).
Hurlstone and Clevers. EMBO J. 21, 2303-2311 (2002).
Itoh, et al., Eur J Biochem 267, 6954-67 (2000).
Itoh, et al., Transplantation 69, 598-604 (2000).
Kandel, and Hay, Exp Cell Res 253, 210-29 (1999).
Kang, et al., J Biol Chem 274, 13085-90 (1999).
Karlin and Altschul. Proc. Natl. Acad. Sci., USA 87:2264-2268. (1993).
Khatri, P., Draghici, S., Ostermeier, G. C. & Krawetz, S. A. Profiling gene expression using onto-express. Genomics 79, 266-270 (2002).
Khwaja, et al., EMBO J. 16, 2783-2793 (1997).
Kimura, et al. Development 130, 1691-1700 (2003).
King, et al., J Biol Chem 278, 11661-9 (2003).
Kobayashi, et al., Biol Pharm Bull 25, 1214-6 (2002).
Kohler and Milstein, "Continuous cultures of fused cells secreting antibody of predefined specificity," Nature, 256: 495-497, 1975.
Kohler and Milstein, "Derivation of specific antibody-producing tissue culture and tumor lines by cell fusion," Eur. J. Immunol., 6:511-519, 1976.
Koike, M. et al. beta-Catenin shows an overlapping sequence requirement but distinct molecular interactions for its bidirectional passage through nuclear pores. J. Biol. Chem. 279, 34038-34047 (2004).
Korinek, et al., Nat Genet. 19, 379-383 1998).
Kuhn, R., Schwenk, F., Aguet, M. & Rajewsky, K. Inducible gene targeting in mice. Science 269, 1427-1429 (1995).
Kwoh et al., Proceedings National Academy of Science 86: 1173-1177 (1989)).
Lapidot, T. et al. A cell initiating human acute myeloid leukaemia after transplantation into SCID mice. Nature 367, 645-648 (1994).
Liaw, D. et al. Germline mutations of the PTEN gene in Cowden disease, an inherited breast and thyroid cancer syndrome. Nat. Genet. 16, 64-67 (1997).
Lim, et al., Neuron 28, 713-726 (2000).
Lin, B. et al. Prostate-localized and androgen-regulated expression of the membrane-bound serine protease TMPRSS2. Cancer Res. 59, 4180-4184 (1999).
Lowry, W. E. et al. Defining the impact of β-catenin/Tcf transactivation on epithelial stem cells. Genes Dev. 19, 1596-1611 (2005).
Luongo, et al., Cancer Res 54, 5947-5952 (1994).
Maehama and Dixon. J Biol Chem 273, 13375-8 (1998).
Maggio. Ed., Enzyme-Immunoassay, CRC Press, Florida, 1980.
Massague. Annu Rev Biochem 67, 753-91 (1998).
McMahon, et al., Genes Dev 12, 1438-1452 (1998).
Megy, S. et al. Solution structure of a peptide derived from the oncogenic protein [beta]-Catenin in its phosphorylated and nonphosphorylated states. Peptides 26, 227-241 (2005).
Mishina, et al., Genes Dev 9, 3027-3037 (1995).
Mishina, et al., Genesis 32, 69-72 (2002).
Morrison, et al., Immunity 5, 207-16. (1996).
Munishkin et al., Nature 33: 473 (1988)).
Nagasako, et al., J Biol Chem 278, 4821-4825 (2003).
Nakamura, et al., Biochem Biophys Res Commun 307, 206-13 (2003).
Novak, et at., Genesis 28, 147-155 (2000).
Passegue, E., Wagner, E. F. & Weissman, I. L. JunB deficiency leads to a myeloproliferative disorder arising from hematopoietic stem cells. Cell 119, 431-443 (2004).
Penninger and Woodgett Science 294, 2116-8 (2001). Persad, S., Troussard, A. A., McPhee, T. R., Mulholland, D. J. & Dedhar, S. Tumor suppressor PTEN inhibits nuclear accumulation of beta-catenin and T cell/lymphoid enhancer factor 1-mediated transcriptional activation. J. Cell Biol. 153, 1161-1174 (2001).
Piedra, J. et al. Regulation of beta-catenin structure and activity by tyrosine phosphorylation. J. Biol. Chem. 276, 20436-20443 (2001).
Polakis. Genes Dev 14, 1837-1851 (2000).
Potten and Booth. J Invest Dermatol 119, 888-899 (2002).

Potten, et al., Identification of a putative intestinal stem cell and early lineage marker; musashi-1. Differentiation 71, 28-41 (2003).

Potten, C. S., Owen, G. & Booth, D. Intestinal stem cells protect their genome by selective segregation of template DNA strands. J. Cell Sci. 115, 2381-2388 (2002).

Powell, et al., Nature 359, 235-237 (1992).

Prendergast and Ziff. *Trends Genet.* 8, 91-6 (1992).

Preston, S. L. et al. Bottom-up histogenesis of colorectal adenomas: origin in the monocryptal adenoma and initial expansion by crypt fission. Cancer Res. 63, 3819-3825 (2003).

Quaroni, et al., *Am J Physiol Cell Physiol* 279, C1045-57 (2000).

Radtke, F. & Clevers, H. Self-renewal and cancer of the gut: two sides of a coin. Science 307, 1904-1909 (2005).

Ray, et al. *Proc Natl Acad Sci USA* 100, 6098-103 (2003).

Reya, T., Morrison, S. J., Clarke, M. F. & Weissman, I. L. Stem cells, cancer, and cancer stem cells. Nature 414, 105-111 (2001).

Roberts. Dev Dyn 219, 109-120 (2000).

Sancho, E., Batlle, E. & Clevers, H. Signaling Pathways in Intestinal Development and Cancer. Annu. Rev. Cell Dev. Biol. 20, 695-723 (2004).

Sharma, M., Chuang, W. W. & Sun, Z. Phosphatidylinositol 3-kinase/Akt stimulates androgen pathway through GSK3beta inhibition and nuclear beta-catenin accumulation. J. Biol. Chem. 277, 30935-30941 (2002).

Shih, I. M. et al. Top-down morphogenesis of colorectal tumors. Proc. Natl. Acad. Sci. U.S.A. 98, 2640-2645 (2001).

Singh, S. K. et al. Identification of human brain tumour initiating cells. Nature 432, 396-401 (2004).

Spradling, et al., *Nature* 414, 98-104 (2001).

Stiles, B., Groszer, M., Wang, S., Jiao, J. & Wu, H. PTENless means more. Dev. Biol. 273, 175-184 (2004).

Tao, W. A. et al. Quantitative phosphoproteome analysis using a dendrimer conjugation chemistry and tandem mass spectrometry. Nat Methods 2, 591-598 (2005).

Taurin, S., Sandbo, N., Qin, Y., Browning, D. & Dulin, N. O. Phosphorylation of beta-catenin by cyclic AMP-dependent protein kinase. J. Biol. Chem. 281, 9971-9976 (2006).

Teleman and Cohen. Cell 103, 971-980 (2000).

Tetsu, O. & McCormick, F. Beta-catenin regulates expression of cyclin D1 in colon carcinoma cells. Nature 398, 422-426 (1999).

Tian, Q. et al. Proteomic analysis identifies that 14-3-3{zeta} interacts with {beta}-catenin and facilitates its activation by Akt. Proc. Natl. Acad. Sci. U.S.A. 101, 15370-15375 (2004).

Travers. EMBO Rep 4, 131-6 (2003).

van de Wetering, M. et al. The beta-catenin/TCF-4 complex imposes a crypt progenitor phenotype on colorectal cancer cells. Cell 111, 241-250 (2002).

van Noort, M., Meeldijk, J., van der Zee, R., Destree, O. & Clevers, H. Wnt signaling controls the phosphorylation status of beta-catenin. J. Biol. Chem. 277, 17901-17905 (2002).

Vazquez, et al., Mol Cell Biol 20, 5010-5018 (2000).

Vazquez, F. et al. Phosphorylation of the PTEN tail acts as an inhibitory switch by preventing its recruitment into a protein complex. J. Biol. Chem. 276, 48627-48630 (2001).

Waite, K. A. & Eng, C. BMP2 exposure results in decreased PTEN protein degradation and increased PTEN levels. Hum. Mol. Genet. 12, 679-684 (2003).

Wasan, H. S. et al. APC in the regulation of intestinal crypt fission. J. Pathol. 185, 246-255 (1998).

Weissman. *Cell* 76, 207-218 (1994).

Wice and Gordon. J Biol Chem 273, 25310-25319 (1998).

Wilson, et al., Cancer Res 61, 8803-8810 (2001).

Wong, et al., *Am J Physiol Endocrinol Metab* 284, E972-9 (2003).

Wong, W. M. et al. Histogenesis of human colorectal adenomas and hyperplastic polyps: the role of cell proliferation and crypt fission. Gut 50, 212-217 (2002).

Wu, et al., *Oncogene* 22, 3113-22 (2003).

Yamashita, et al., *Science* 301, 1547-50 (2003).

Yi, et al., Development 127, 621-630 (2000).

Yilmaz, O. H. et al. Pten dependence distinguishes haematopoietic stem cells from leukaemia-initiating cells. Nature 441, 475-482 (2006).

Zhang, et al. *Biochem Biophys Res Commun* 293, 1412-9 (2002).

Zhang, et al. *Nature* 425(6960):836-41 (2003).

Zhang, J. et al. PTEN maintains hematopoietic stem cells and acts in lineage choice and leukaemia prevention. Nature 441, 518-522 (2006).

Zhou, X. P. et al. Germline mutations in BMPR1A/ALK3 cause a subset of cases of juvenile polyposis syndrome and of Cowden and Bannayan-Riley-Ruvalcaba syndromes. Am. J. Hum. Genet. 69, 704-711 (2001).

DEPOSIT

The polyclonal anti-p-beta-cat-Ser552 antibody of the invention was deposited with the Patent Depository of the American Type Culture Collection, 10801 University Blvd., Manassas, Va. 20110-2209, USA (ATCC) on Mar. 13, 2008 and assigned Patent Deposit Designation No. PTA-9077.

What is claimed is:

1. A purified antibody that binds specifically to β-catenin phosphorylated at amino acid position Serine$^{552}$, wherein the antibody specifically binds to an epitope that is within the sequence HQDTQRRTSMGG (SEQ ID NO:5).

2. The purified antibody according to claim 1, wherein the antibody is monoclonal.

3. The purified antibody according to claim 1, wherein the antibody is polyclonal.

4. The purified antibody according to claim 1, wherein the antibody is a human, mouse, rabbit, or rat antibody.

5. A purified antibody that binds specifically to β-catenin phosphorylated at amino acid position Serine$^{552}$, wherein the antibody binds to an epitope that is within the sequence QDTQRRTSMGGTQQQ (SEQ ID NO:4).

6. The purified antibody according to any one of claims 1 or 5, which specifically binds to a human ortholog phosphorylated at amino acid position Serine$^{552}$.

7. The purified antibody according to claim 5, wherein the antibody is monoclonal.

8. The purified antibody according to claim 5, wherein the antibody is polyclonal.

9. The purified antibody according to claim 5, wherein the antibody is a human, mouse, rabbit, or rat antibody.

10. A purified antibody that binds to a polypeptide consisting of SEQ ID NO:4.

11. A purified antibody that binds to a polypeptide consisting of SEQ ID NO:5.

12. An anti-p-beta-cat-Ser$^{552}$ antibody deposited with ATCC under accession number PTA-9077.

13. A kit for detecting phosphorylation at Serine$^{552}$ of β-catenin comprising a purified antibody that binds specifically to β-catenin phosphorylated at amino acid position Serine$^{552}$, wherein the antibody binds to an epitope within SEQ ID NO: 4 or SEQ ID NO:5, and instructions on how to use the antibody.

14. The kit according to claim 13, wherein the antibody is labeled.

15. The kit according to claim 13, wherein the antibody is an antibody deposited with the ATCC under accession number PTA-9077.

* * * * *

UNITED STATES PATENT AND TRADEMARK OFFICE
CERTIFICATE OF CORRECTION

PATENT NO. : 8,106,166 B2  Page 1 of 1
APPLICATION NO. : 12/077290
DATED : January 31, 2012
INVENTOR(S) : Xi He et al.

It is certified that error appears in the above-identified patent and that said Letters Patent is hereby corrected as shown below:

Cover Page:

Item 54 and Col. 1, line 1

In the TITLE, please change "ANTIBODIES THAT BIND" to -- ANTIBODY THAT BINDS --

Signed and Sealed this
Twenty-fourth Day of April, 2012

David J. Kappos
*Director of the United States Patent and Trademark Office*